United States Patent
Kessler et al.

(10) Patent No.: US 10,488,332 B2
(45) Date of Patent: Nov. 26, 2019

(54) DEVICE AND METHOD FOR DETERMINING THE DIRT LOAD IN A RINSING OR DETERGENT SOLUTION

(71) Applicants: BSH Hausgeräte GmbH, Munich (DE); Henkel AG & Co.KGaA, Düsseldorf (DE)

(72) Inventors: Arnd Kessler, Monheim am Rhein (DE); Edith Lambert, Bonn (DE); Nina Mußmann, Willich (DE); Rainer Stamminger, Bonn (DE); Thomas Weber, Dormagen (DE); Michaela Gerstenlauer, Blindheim (DE); Heinz Heißler, Dillingen (DE); Martin Stickel, Giengen (DE)

(73) Assignees: BSH Hausgeräte GmbH, Munich (DE); Henkel AG & Co. KGaA, Düsseldorf (DE)

(*) Notice: Subject to any disclaimer, the term of this patent is extended or adjusted under 35 U.S.C. 154(b) by 0 days.

(21) Appl. No.: 15/577,359

(22) PCT Filed: Apr. 29, 2016

(86) PCT No.: PCT/EP2016/059648
§ 371 (c)(1),
(2) Date: Nov. 28, 2017

(87) PCT Pub. No.: WO2016/188705
PCT Pub. Date: Dec. 1, 2016

(65) Prior Publication Data
US 2018/0156725 A1  Jun. 7, 2018

(30) Foreign Application Priority Data

May 28, 2015 (DE) .......................... 10 2015 209 824

(51) Int. Cl.
*A47L 15/42* (2006.01)
*G01N 21/3577* (2014.01)
(Continued)

(52) U.S. Cl.
CPC ...... *G01N 21/3577* (2013.01); *A47L 15/4297* (2013.01); *C11D 3/386* (2013.01);
(Continued)

(58) Field of Classification Search
CPC ............. G01N 21/3577; A47L 15/4297; A47L 15/449; A47L 15/4445; A47L 15/4463;
(Continued)

(56) References Cited

U.S. PATENT DOCUMENTS 5,083,447 A * 1/1992 Kiuchi ................. G01N 21/534
  68/12.02
5,881,578 A   3/1999 Proppe et al.
(Continued)

FOREIGN PATENT DOCUMENTS

CN     102720034 A   10/2012
CN     105147216 A   12/2015
(Continued)

OTHER PUBLICATIONS

Report of Examination DE 10 2015 209 824.9 dated Feb. 12, 2016.
International Search Report PCT/EP2016/059648 dated Sep. 29, 2016.

*Primary Examiner* — Michael E Barr
*Assistant Examiner* — Tinsae B Ayalew
(74) *Attorney, Agent, or Firm* — Michael E. Tschupp; Andre Pallapies; Brandon G. Braun

(57) ABSTRACT

A device for determining a dirt load in a rinsing or detergent solution in a water-conducting household appliance includes a sensor configured to execute a near-infrared spectroscopy for acquiring a spectral measured value of a dirt component (Continued)

in the rinsing or detergent solution in the water-conducting household appliance. A determination unit determines the dirt load of the rinsing or detergent solution on the basis of the acquired spectral measured value of the dirt component in the rinsing or detergent solution, and an adjustment unit adjusts a wash parameter of a current wash program in response to the determined dirt load.

26 Claims, 7 Drawing Sheets

(51) Int. Cl.
| | | |
|---|---|---|
| C11D 3/386 | (2006.01) | |
| D06F 39/00 | (2006.01) | |
| C11D 11/00 | (2006.01) | |
| G01N 21/359 | (2014.01) | |

(52) U.S. Cl.
CPC ...... *C11D 3/38627* (2013.01); *C11D 11/0017* (2013.01); *C11D 11/0023* (2013.01); *D06F 39/004* (2013.01); *G01N 21/359* (2013.01)

(58) Field of Classification Search
CPC ............ A47L 2401/10; A47L 2501/01; A47L 2501/03; A47L 2501/05; A47L 2501/06; A47L 2501/07; A47L 2501/30; C11D 3/386; C11D 3/38627; C11D 11/0017; C11D 11/0023; D06F 39/004; D06F 39/022
USPC ....................................... 134/56 D
See application file for complete search history.

(56) References Cited

U.S. PATENT DOCUMENTS

| | | | | |
|---|---|---|---|---|
| 5,889,192 | A | * 3/1999 | Engel | ................. A47L 15/4297 73/1.02 |
| 6,464,798 | B1 | 10/2002 | Rosenbauer et al. | |
| 2001/0049846 | A1 * | 12/2001 | Guzzi | ..................... D06F 33/02 8/158 |
| 2004/0216774 | A1 | 11/2004 | Bertram et al. | |
| 2009/0056754 | A1 * | 3/2009 | Rolek | ................. A47L 15/0018 134/18 |
| 2010/0012160 | A1 * | 1/2010 | Jeong | ................. A47L 15/4204 134/111 |
| 2011/0290281 | A1 | 12/2011 | Kessler et al. | |
| 2012/0264672 | A1 | 10/2012 | Bastigkeit et al. | |
| 2013/0036772 | A1 | 2/2013 | Brueckner et al. | |
| 2013/0042652 | A1 | 2/2013 | Brueckner et al. | |
| 2015/0099682 | A1 | 4/2015 | Mussmann et al. | |

FOREIGN PATENT DOCUMENTS

| | | |
|---|---|---|
| DE | 102008007429 A1 | 8/2009 |
| EP | 1595137 B1 | 4/2010 |
| EP | 2528487 B1 | 3/2017 |
| JP | 2009240546 A | 10/2009 |
| JP | 2010223871 A | 10/2010 |
| JP | 2014014561 A | 1/2014 |
| KR | 100773645 B1 | 11/2007 |
| WO | 2005058126 A | 6/2005 |
| WO | 2008019902 A1 | 2/2008 |
| WO | 2011110243 A1 | 9/2011 |

* cited by examiner

DEVICE AND METHOD FOR DETERMINING THE DIRT LOAD IN A RINSING OR DETERGENT SOLUTION

CROSS-REFERENCES TO RELATED APPLICATIONS

This application is the U.S. National Stage of International Application No. PCT/EP2016/059648, filed Apr. 29, 2016, which designated the United States and has been published as International Publication No. WO 2016/188705 A1 and which claims the priority of German Patent Application, Serial No. 10 2015 209 824.9, filed May 28, 2015, pursuant to 35 U.S.C. 119(a)-(d).

BACKGROUND OF THE INVENTION

The present invention relates to a device and a method for determining the dirt load in a rinsing or detergent solution in a water-conducting household appliance, e.g. in a dishwasher. The invention further relates to a water-conducting household appliance incorporating such a device. The invention also relates to methods for cleaning wash items in a water-conducting household appliance and to the use of detergent product formats in combination with the methods described here.

In water-conducting household appliances such as dishwashers, for example, it is possible to react to differences in respect of the quantity and kinetics of the dirt load in the rinsing or detergent solution, which correlates with the soiling of the wash items, with the aid of sensors, in particular optical sensors, which typically measure the turbidity of the rinsing or detergent solution. The wash parameters can be adjusted according to the degree of turbidity detected. A sensor system of this kind combined with an appropriately designed dosing device is disclosed, for example, in the publication WO 2011/110243 A1. In addition, the publication WO 2005/058126 A1 discloses a dishwasher incorporating a dosing device for dispensing additives, e.g. into the wash tub of the dishwasher. Here at least one base chemical not used for rinsing and/or at least two base chemicals together, but not all the chemicals of an all-round product together, and/or at least one reaction mixture of base chemicals can be added independently.

However, the existing technology does not allow the dirt load in the rinsing or detergent solution to be adequately characterized, particularly in terms of detecting dirt components particularly relevant to the cleaning process, such as greasy, starchy or protein-containing soilings, particularly in isolation. As the different dirt components also require different constituents of the detergent or cleaning agent used in order to ensure efficient cleaning, it is desirable to provide more specific sensing so that dosing rules in the washing or rinsing process can then be derived therefrom. The lack of such a possibility in existing systems means that the user's desired cleaning outcome is often not achieved.

In addition, the disadvantage of the currently used optical measuring systems which determine the turbidity of the detergent solution/wash water is that they cannot differentiate between turbidity levels caused by dispersed soiling from the wash load, residual dirt from the machine, particularly the machine sump, turbidity levels caused by the detergent used or deposits such as limescale. There is therefore also a need to provide improved optical sensor systems that are able to differentiate between the actual dirt load and other factors affecting the turbidity of the water.

BRIEF SUMMARY OF THE INVENTION

Against this background, the object of the present invention is to provide improved detection of the dirt load in a rinsing or detergent solution in a water-conducting household appliance.

Accordingly, in a first aspect, a device for determining the dirt load in a rinsing or detergent solution in a water-conducting household appliance is proposed. The device has a sensor for acquiring spectral measured values of dirt components in the rinsing or detergent solution in the water-conducting household appliance using near-infrared (NIR) spectroscopy, a determination unit for determining the dirt load of the rinsing or detergent solution, based on the acquired spectral measured values of the rinsing or detergent solution, and an adjustment unit for adjusting wash parameters of a current wash program, based on the dirt load determined.

The device is based on the principle, not of determining the turbidity of the rinsing or detergent solution, but of specifically determining the amount and preferably also the type of soiling in the rinsing or detergent solution, i.e. the individual dirt components. In this way the soiling of the wash items can be determined indirectly in respect of individual dirt components. The device can therefore be used to ascertain the removal rate of the soiling, i.e. to determine how much and what soiling is being removed from the wash items.

The proposed device provides improved detection in respect of the nature, quantity and kinetics of the soiling of wash items in a water-conducting household appliance. In this way, optimized cleaning can be performed for the user of a water-conducting household appliance in an optimally resource-saving manner.

In this context, a water-conducting household appliance can be understood as meaning, for example, a dishwasher with dishes as wash items or a washing machine with fabrics as wash items. Rinsing or detergent solution, as used here, means an aqueous liquid including the totality of all its components, i.e. the solvent (mainly water) and all the dissolved, emulsified or dispersed components contained therein which are used to treat wash items such as, for example, dishes in a dishwasher or laundry items in a washing machine, usually for the purpose of cleaning/washing them. The rinsing or detergent solution therefore typically contains water and the therein contained constituents of a detergent or cleaning agent, as well as dirt components. Where a multi-stage cleaning process is used, the term embraces the liquids used in all the stages of the process. Dirt load is to be understood here as meaning the totality of the soilings in a given medium, typically the rinsing or detergent solution. Soilings denotes the totality of all the dirt components. The main constituents of the soilings in dishwashing or fabric washing are fats, proteins and starch. The main constituents are in turn composed of a plurality of organic compounds which are all subsumed under the general term of the component. According to the invention, these organic compounds can be both qualitatively and quantitatively determined in the rinsing or detergent solution by means of NIR. Determining the dirt load therefore also includes individual determination of the type and/or amount of the individual dirt components, or more specifically of the organic compounds constituting them.

The sensor used is designed to employ near-infrared spectroscopy, hereinafter also referred to as NIR. Depending on requirements, the complete NIR region can be covered or only individual specific wavelengths can be measured and considered. These measured wavelengths are also termed spectral measured values.

The NIR measurement detects, for example, a wavelength or wavelength range between 800 and 2500 nm or rather a wavenumber or wavenumber range between 12500 and 4000 $cm^{-1}$. NIR spectroscopy is a form of vibrational spectroscopy based on the excitation of molecular vibrations by electromagnetic radiation in the near-infrared region. In this region, overtone and combination vibrations of the fundamental vibration are excited. The molecular vibrations occurring can be valence vibrations, i.e. changes in the bond length of the molecules, or deformation vibrations, i.e. changes in the bond angle of the molecules. NIR is particularly suitable for analyzing organic compounds, as it enables functional groups of organic compounds, such as the C—H, O—H, N—H, C=O, $CH_2$, $CH_3$ groups, for example, to be identified. As each molecule has a specific absorption profile based on the presence of functional groups, NIR can be used to determine particular compounds or substance classes.

NIR measurement is fast and relatively low-cost compared to measurements in the MWIR (mid-wavelength infrared) or FIR (far-infrared) range. Moreover, an NIR measurement is non-destructive and requires minimal sample preparation. Compared to other methods, NIR measurement has a relatively great penetration depth. Liquids, i.e. the rinsing or detergent solution, can be measured undiluted, there being only slight attenuation on glass. The rinsing or detergent solution measured and the sensor can therefore be physically separate.

NIR is used among other things in agriculture, food chemistry or pharmacy in order to determine, for example, water, starch, fat, proteins, alcohol content or sugar content in foodstuffs and medicines.

The NIR measurement of the sensor can be used to acquire the spectral measured values of organic compounds in the rinsing or detergent solution. Based on these measured values, the determination unit can detect the amount and type of organic compounds and therefore the type of soiling currently (still) present.

On the basis of the soiling determined, wash parameters of a current wash program can then be adjusted by the adjustment unit. As the sensor determines the dirt load in the rinsing or detergent solution, i.e. indirectly the soiling on the wash items, the wash parameters are controlled by the adjustment unit on the basis of the type of individual components found combined with the quantity and time in the wash water.

Wash parameters can be, for example, temperatures, speeds, changes between different spray levels (defined time at a level in order to find the level in which dirt removal is still possible), times, water quantities, number of cleaning and/or rinsing baths, baths heated or unheated, drain pumping mechanisms, adding of additional or individual detergent components, etc. These wash parameters can depend on other general conditions which may already be preset. These general conditions include, for example, resource saving, speed or fabric care.

According to one embodiment, the sensor is designed to carry out a transmission measurement and/or a reflection measurement.

In the case of a transmission measurement, the radiation that penetrates the dirt molecules, i.e. organic compounds, present in the rinsing or detergent solution is determined. In the case of a reflection measurement, the radiation reflected by the molecules is measured. A combination of both measurements is possible.

In the case of a pure transmission measurement, the sensor can be protected from solids by a filter device or by a filter system in order to optimize the measurement. The transmission measurement can be performed, for example, by means of a flow cell of suitable film thickness, possibly also in the form of a probe.

According to another embodiment, for determining the dirt load, the determination unit is designed to determine a plurality of different dirt components within the dirt load. These are in particular the three basic constituents of the dirt: fat, protein and starch.

According to another embodiment, the determination device is designed to compare output data of the sensor with a predefined calibration model.

For this purpose, known samples can be measured in advance and a link established using chemometric analysis methods. A calibration model of this kind can then be used to determine unknown samples on the basis of the NIR spectrum during a wash program.

Based on the dirt components determined, a characteristic picture of the entire wash process can be created, i.e. changes in the soiling of the wash items based on the type and quantity of dirt components in the rinsing or detergent solution. Using this information it is possible to specifically adjust and optimize wash programs. A wide range of scenarios is possible depending on the characteristic detected.

According to another embodiment, the calibration model contains a plurality of different items of spectral information with associated organic compounds.

The calibration model can contain different items of spectral information. Comparison of the spectral measured values obtained by the sensor against this spectral information can provide an indication of particular organic compounds, i.e. particular dirt components. The adjustment unit can then, for example, adjust the program sequence, e.g. by adjusting the wash parameters, via already predefined threshold values. The predefined threshold values can likewise be contained in the calibration model.

The spectral information is available as information about the absorption of particular dirt components in narrow wavelength ranges or individual bands. Possible spectral regions for determining fats as dirt components in the rinsing or detergent solution are in particular spectral regions in the wavenumber range from 10803 to 7405 $cm^{-1}$, from 5990 to 5334 $cm^{-1}$ and/or from 4875 to 4104 $cm^{-1}$, in particular from 6990 to 5388 $cm^{-1}$, from 4860 to 4130 $cm^{-1}$ and/or from 4400 to 4200 $cm^{-1}$. Wavenumber regions suitable for indicating proteins are in the range from 6904 to 5326 $cm^{-1}$ and/or from 4655 to 4543 $cm^{-1}$, in particular from 6570 to 6200 $cm^{-1}$, from 5840 to 5760 $cm^{-1}$, from 5410 to 5346 $cm^{-1}$ and/or from 4655 to 4555 $cm^{-1}$. Possible spectral regions for indicating starch are in the range from 9947 to 7849 $cm^{-1}$ and/or from 4802 to 4273 $cm^{-1}$, in particular from 8800 to 8700 $cm^{-1}$ and/or from 4787 to 4302 $cm^{-1}$. For each of the above-mentioned dirt components, a plurality of the specified spectral regions can be combined, particularly also in order to enable the dirt component to be identified as unambiguously as possible in the case of overlapping regions.

Determination of the dirt load can include on the one hand identification of the dirt components on the basis of the spectral measured values and possibly comparison with a calibration model. Alternatively or additionally, however, determination of the dirt load can also be used to determine the dirt removal rate. In doing so, the variation over time, possibly in conjunction with other information such as temperature, time, etc., provides an indication of the washing/cleaning performance of the appliance or rather of the appliance program. Thus, for example, if no further change in a given signal is detectable, the cleaning process can be deemed to be complete in respect of the dirt component determined using that signal. In particular embodiments, predefined threshold values must be reached, e.g. a minimum temperature, in order to make sure that a greasy soiling is present in liquefied form.

According to another embodiment, the adjustment unit is designed to adjust the current wash program on the basis of a user input.

The current wash program can basically be adjusted on the basis of the determined soiling or of the dirt removal rate as described above. As already described above, the adjustment can take place based on measured values in respect of the type and amount of soiling or the amounts of particular dirt components relative to one another, but also on changes over time in the dirt removal rate (increase, stagnation, decrease of the dirt load). Detecting the removal rate of e.g. proteins or starch enables enzyme phases to be strengthened, for example. In addition, irrespective of the detergent used, weaknesses (of the detergent) can be compensated by strengths of the program structure and the potential of powerful detergents can be utilized through savings in the program structure, e.g. reducing the program run time, the temperature used or the amount of water. This also makes it possible to compensate detergent aging. The removal rate can be optimized by adjusting the temperature, speed, time, adding of detergent, etc. The emulsifiability of fats can likewise be improved by, for example, adjusting the temperature of the rinsing or detergent solution or adding more detergent. Dirt removal can be optimized by adjusting the number and/or sequence of individual bath structures: one or more cleaning baths and/or intermediate wash baths, heated or unheated according to requirements.

According to one embodiment, based on the determined soiling or dirt removal rate, the adjustment unit can vary the wash program in terms of increasing or reducing the wash time, increasing or reducing the temperature, carrying out or omitting an additional water change, adding detergent or detergent components, or changing mechanical wash variables such as the spray strength or the manner in which the rinsing or detergent solution is circulated, for example.

Adjustment of the addition of the detergent used, either as a complete composition or in the form of individual constituents or in the form of specific formulations for particular dirt components, can take place in per se known manner. Suitable dosing systems for detergents, particularly for dishwashers and washing machines which respond to a signal, in particular a measurement signal, as well as various suitable detergent formulations are described in the publications WO 2010/031607 A1, WO 2010/031605 A1, WO 2010/006761 A2 and WO 2009/146692 A2, WO 2011/110243 A1 and WO 2005/058126 A1, for example; their relevant disclosure content is herewith made the subject matter of the present description. Detergent formulations in which the individual components are provided separately offer advantages in terms of stability, costs, ease of dosing or the possibility of dosing in different ratios. Such detergent systems can be provided, for example, in the form of cartridges, possibly matched to the respective machine, as likewise described in the above-mentioned publications.

Such dosing systems for multiple dosing of detergents are well known and for these devices a distinction can be drawn between dosing systems incorporated in the dishwasher or washing machine on the one hand and, on the other, separate and movable dosing systems independent of the dishwasher or washing machine. By means of these dosing systems which contain multiple doses of the amount of detergent required for carrying out an individual wash, detergent portions are automatically or semi-automatically dosed from a cartridge into the interior of the machine by a dosing device over a plurality of consecutive washes. This relieves the user of the need to repeatedly add detergent manually. Examples of such devices are described in the publications EP 1 759 624 A2, EP 1 976 970 A1, DE 10 2005 062 479 A1 or WO 2005/058126 A1; their relevant disclosure content is herewith made the subject matter of the present description.

In the devices and methods of the invention, a detergent formulation is dosed by means of a storage device inside the water-conducting household appliance over a plurality of wash cycles.

The inventively used adjustment unit can additionally take user inputs into account. For example, a user may want a water-saving, energy-saving or time-saving program. This can then be taken into account for the adjustment. In addition, the user can preset the type of items to be washed, such as particularly greasy items, for example.

In one embodiment, it can also be provided that the user does not select a wash program but can only determine additional options. The selection of the appropriate wash program, or rather the control and adjustment of the wash program, then takes place only via the sensor, the determination unit and the adjustment unit.

According to another embodiment, the sensor is designed to measure the organic compounds at a defined temperature.

As the NIR measurement is temperature-dependent, according to this embodiment the measurement can take place during a defined temperature.

According to another embodiment, the sensor is designed to measure the organic compounds using a correction factor.

Instead of a defined temperature, the measured value acquired can be adjusted via a correction factor at different temperatures in order to avoid misinterpretations.

According to another embodiment, the sensor is disposed in a pump sump of the water-conducting household appliance or in a bypass arrangement inside and/or outside a wash tub of the water-conducting household appliance. The determination and adjustment unit can then likewise be disposed inside and/or outside the water-conducting household appliance. If the adjustment unit is a dosing system for detergent or detergent components, in particular embodiments at least parts thereof need not be built-in, but can be externally loaded in the form of a cartridge. Corresponding dosing systems are described, for example, in the above-cited publications WO 2010/031607 A1, WO 2010/031605 A1, WO 2010/006761 A2, WO 2009/146692 A2, WO 2011/110243 A1 and WO 2005/058126 A1.

If the sensor is disposed in the pump sump, it is mounted in a non-turbulent part of the rinsing or detergent solution in which a stable measurement is possible. In addition, if required, the speed can be set to a predefined level during the measurement. The sensor can be protected from solid particles via a filter system of some kind. The hole size of the filter and the flow rate are designed to prevent in particular any accumulation of solid particles over the wash cycle.

The sensor can also be mounted in bypass of some kind. General conditions other than those inside the washer can be created in said bypass. These include, for example, a defined flow rate (without affecting the wash cycle by reducing the speed) or the setting of a suitable temperature. Such a bypass can extend, for example, from the outlet of the liquor reservoir into the pump sump below the sieve.

According to one embodiment, the sensor is disposed in the water-conducting household appliance. In addition, a water-conducting household appliance is proposed which has a device as described above for determining a soiling of wash items in the water-conducting household appliance.

According to one embodiment, the water-conducting household appliance is a dishwasher or a washing machine.

According to another embodiment, the device for determining a soiling of wash items is designed to communicate with an external server.

The external server can comprise a database. The device can communicate with the external server via an Internet connection, wired or wireless.

According to another embodiment, the device for determining a soiling of wash items is designed to transmit the detected organic compounds and/or the particular soiling of the wash items to the external server.

The transmitted information can be stored in the database of the external server. Moreover, the information can be used to optimize wash processes.

According to another embodiment, the water-conducting household appliance is designed to receive a program update from the external server.

The transmitted information can be used to optimize wash programs which can then be taken into account in a program update. Such an update can be directly imported into the water-conducting household appliance via an Internet connection.

In addition, calibration models can be received by the external server. These can be adapted on a country-specific basis, for example. A country-specific calibration model can contain, for example, country-specific foods, dirt and/or soiling.

The embodiments and features described for the proposed device apply correspondingly to the method proposed below.

In another aspect, a method for determining the dirt load in a rinsing or detergent solution in a water-conducting household appliance is proposed. The method comprises the following steps: acquiring spectral measured values of dirt components in the rinsing or detergent solution in the water-conducting household appliance using near-infrared spectroscopy, and determining the dirt load of the rinsing or detergent solution based on the acquired spectral measured values of the organic compounds.

Another aspect of the invention relates to a method for cleaning wash items, in particular dishes or fabrics, in a water-conducting household appliance, in particular a dishwasher or a washing machine, comprising:
  acquiring spectral measured values of dirt components in a rinsing or detergent solution in the water-conducting household appliance using near-infrared spectroscopy;
  determining the dirt load of the rinsing or detergent solution based on the acquired spectral measured values of the dirt components; and
  adjusting wash parameters of a current wash program based on the particular dirt load, wherein the wash parameters are selected from changing the wash time, the temperature, the number of water changes carried out, and mechanical wash variables.

Another aspect of the invention relates to methods for cleaning wash items, in particular dishes or fabrics, in a water-conducting household appliance, in particular a dishwasher or a washing machine, comprising:
  acquiring spectral measured values of dirt components in a rinsing or detergent solution in the water-conducting household appliance using near-infrared spectroscopy;
  determining the dirt load of the rinsing or detergent solution based on the acquired spectral measured values of the dirt components; and
  detergent dosing based on the dirt load determined.

In various embodiments of the invention, the method is carried out using a multicomponent product format, comprising at least two, preferably all three of:
a) a preferably liquid detergent formulation A, containing at least one constituent having a cleaning effect on starchy soilings, particular an amylase;
b) a preferably liquid detergent formulation B, containing at least one constituent having a cleaning effect on protein-containing soilings, in particular a protease; and
c) a preferably liquid detergent formulation C, containing at least one constituent having a cleaning effect on greasy soilings, in particular a lipase or at least one nonionic surfactant.

In the course of the cleaning process, preferably a dishwashing or fabric washing process, the detergent formulations A, B and C can be dispensed into the interior of the machine from a cartridge preferably located inside the water-conducting household appliance. A portion a of the detergent formulation A contained in the cartridge is dispensed into the interior of the machine, a residual amount of the detergent formulation A contained in the cartridge remaining in the cartridge until the end of the process and said residual amount corresponding to at least twice, preferably at least four times and in particular at least eight times the amount of the portion a; and/or a portion b of the detergent formulation B contained in the cartridge is dispensed into the interior of the machine, a residual amount of the detergent formulation B contained in the cartridge remaining in the cartridge until the end of the process and said residual amount corresponding to at least twice, preferably at least four times and in particular at least eight times the amount of the portion b; and/or a portion c of the detergent formulation C contained in the cartridge is dispensed into the interior of the machine, a residual amount of the detergent formulation C contained in the cartridge remaining in the cartridge until the end of the process and said residual amount corresponding to at least twice, preferably at least four times and in particular at least eight times the amount of the portion c.

As well as the detergent formulations A, B and C, the detergent product format can comprise one, two or more other detergent formulations, e.g. another detergent formulation D. These two, three or more detergent formulations are preferably present in a common cartridge and are separated from one another. Inventive methods, in particular mechanical dishwashing or fabric washing methods characterized in that detergent formulations A, B and C are separately present in a common cartridge are preferred. The common packaging of the detergent formulations in a common cartridge simplifies the manufacture and handling of the detergent formulation. If the detergent formulations are packaged in the common cartridge such that the mutually separate detergent formulations A, B and C are adjacent to one another, i.e. the accommodation compartments used for packaging the detergent formulations A, B and C have at least one common wall, the packaging of the detergent formulations in a common cartridge is also suitable for increasing the chemical and physical stability of said detergent formulations and, for example, reducing the disadvantageous effect of temperature variations necessarily occurring.

The methods are used in particular for repeated dispensing of detergent formulations from storage containers inside the machine. Preferred methods according to the invention are characterized in that, prior to being dispensed into the interior of the machine, a portion of the preferably liquid detergent formulations A, B and C remains in the storage container inside the machine for the duration of at least two, preferably at least four, with particular preference at least eight and in particular at least twelve separate washes.

In the context of the present invention, "separate washes" denotes completed wash operations which can preferably include, in addition to the main wash cycle, also a pre-wash and/or a rinse and which can be selected and initiated by means of a dishwasher's program switch. The duration of these separate washes is preferably at least 15 minutes, preferably between 20 and 360 minutes, preferably between 30 and 240 minutes.

The time interval between two separate washes within which the liquid detergent formulation is dispensed into the interior of the machine is at least 20 minutes, preferably at least 60 minutes, with particular preference at least 120 minutes.

With regard to the cleaning effect of the inventive methods, the dosing of the two, three or more detergent formulations can take place at different times in the course of the operation.

In one embodiment, enzyme granulates (preferably fine grained) can be used. The advantage of this is that the enzymes are less sensitive to the temperature fluctuations in the machine, i.e. have better temperature stability.

According to a preferred embodiment, the detergent formulations used in the inventive method are preferably liquid. This facilitates precise dosing of the formulations. These formulations preferably contain water as a main solvent. The addition of water to the detergent formulations A, B and C not only facilitates the dosing thereof, but the water content also accelerates the release of the active cleaning ingredients into the rinsing or detergent solution.

The detergent formulations A, B and optionally also C preferably used according to the invention contain at least one detergent enzyme formulation as a basic constituent. The percentage by weight of said enzyme formulations(s) with cleaning action in the total detergent formulation is preferably 2 to 60 wt %, preferably 5 to 50 wt % and in particular 10 to 40 wt %. For the detergent formulation A, particularly enzyme formulations from the group of amylase formulations, are used as enzyme formulations with cleaning action. Similarly, for the detergent formulations B and C, particularly enzyme formulations from the group of protease and lipase formulations respectively are used as enzyme formulations with cleaning action. Lipases are to be understood as meaning lipases in the narrower sense (breaking down glycerol fatty acid esters) as wells as cutinases, phospholipases and other fat or wax hydrolyzing enzymes.

In addition to those mentioned, other enzymes can be contained in each of the formulations. Aside from said proteases, amylases and lipases, enzymes used with particular preference also include hemicellulases, cellulases, perhydrolases or oxidoreductases, as well as mixtures thereof.

All of these enzymes are basically of natural origin; based on the natural molecules, improved variants are available for use in detergents, which variants are accordingly preferably used.

Examples of inventively usable amylases are the α-amylases from *Bacillus licheniformis*, from *B. amyloliquefaciens*, from *B. stearothermophilus*, from *Aspergillus niger* and *A. oryzae* as well as the improved further developments of the above mentioned amylases for use in detergents. In addition, the α-amylase from *Bacillus* sp. A 7-7 (DSM 12368) and the cyclodextrin glucanotransferase (CGTase) from *B. agaradherens* (DSM 9948) are worthy of mention for this purpose.

As regards the proteases, those of the subtilisin type are preferred. Examples of same are the subtilisins BPN' and Carlsberg and their further-developed forms, the protease PB92, the subtilisins 147 and 309, the alkaline proteases from *Bacillus lentus*, subtilisin DY and the enzymes thermitase, proteinase K to be assigned to the subtilases, but no longer to the subtilisins in the narrower sense, and the proteases TW3 and TW7.

Detergent proteases and amylases are not generally provided in the form of the pure protein but rather in the form of stabilized, storable and transportable formulations. These pre-packaged formulations include, for example, the solid preparations obtained by granulation, extrusion or freeze-drying or, particularly in the case of liquid or gel-like agents, solutions of the enzymes, preferably concentrated as far as possible, with low water content and/or admixed with stabilizers or other auxiliary agents.

As can be seen from the above statements, the enzyme protein accounts for only a fraction of the total weight of usual enzyme formulations. Protease, amylase and lipase formulations preferably used according to the invention contain between 0.1 and 40 wt %, preferably between 0.2 and 30 wt %, with particular preference between 0.4 and 20 wt % and in particular between 0.8 and 10 wt % of the enzyme protein. The protein concentration can be determined using known methods, e.g. the BCA assay or biuret test.

Also usable according to the invention are lipases, particularly because of their triglyceride splitting activities. These include, for example, the lipases originally obtainable from *Humicola lanuginosa* (*Thermomyces lanuginosus*), i.e. further-developed lipases, particularly those having one or more of the following amino acid exchanges starting from the said lipase in the positions D96L, T213R and/or N233R, with particular preference all of the exchanges D96L, T213R and N233R.

Enzymes subsumed under the term hemicellulases can also be used. These include, for example, mannanases, xanthanlyases, pectinlyases (=pectinases), pectinesterases, xyloglucanases (=xylanases), pullulanases and β-glucanases.

Alternatively to the enzyme component(s), or also additionally, the detergent formulation C can contain at least one nonionic surfactant. Preferred nonionic surfactants are nonionic surfactants of the general formula $R^1$—CH(OH)CH$_2$O-(AO)$_w$-(A'O)$_x$-(A"O)$_y$-(A'''O)$_z$—$R^2$, in which $R^1$ stands for a straight-chain or branched, saturated or mono- or poly-unsaturated $C_{6-24}$ alkyl or alkenyl residue;

$R^2$ stands for a linear or branched hydrocarbon residue with 2 to 26 carbon atoms;

A, A', A" and A''' stand independently of one another for a residue from the group —CH$_2$CH$_2$, —CH$_2$CH$_2$—CH$_2$, —CH$_2$—CH(CH$_3$), —CH$_2$—CH$_2$—CH$_2$—CH$_2$, —CH$_2$—CH(CH$_3$)—CH$_2$, —CH$_2$—CH(CH$_2$—CH$_3$), w, x, y and z stand for values between 0.5 and 120, where x, y and/or z can also be 0.

In preferred liquid detergent formulations C, the percentage by weight of these nonionic surfactants, referred to the total weight of the detergent formulation B, is 0.5 to 30 wt %, preferably 2.0 to 25 wt % and in particular 5.0 to 20 wt %.

By the addition of the above mentioned nonionic surfactants of the general formula $R^1$—CH(OH)CH$_2$O-(AO)$_w$-(A'O)$_x$-(A''O)$_y$-(A'''O)$_z$—$R^2$, hereinafter also referred to as "hydroxy mixed ethers", the cleaning power of enzyme-containing formulations can be significantly improved, both compared to surfactant-free systems and to systems containing alternative nonionic surfactants, e.g. from the polyalkoxylated fatty alcohols.

Through the use of these nonionic surfactants with one or more free hydroxyl groups on one or both terminal alkyl residues, the stability of the enzymes contained in the detergent formulations according to the invention can be significantly improved.

Preferred are, in particular, closed-terminal-group poly(oxyalkylated) nonionic surfactants, which, according to the formula $R^1O[CH_2CH_2O]_xCH_2CH(OH)R^2$, in addition to the residue $R^1$ which stands for linear or branched, saturated or unsaturated, aliphatic or aromatic hydrocarbon residues with 2 to 30 carbon atoms, preferably with 4 to 22 carbon atoms, also have a linear or branched, saturated or unsaturated, aliphatic or aromatic hydrocarbon residue $R^2$ with 1 to 30 carbon atoms, where x stands for values between 1 and 90, preferably for values between 30 and 80 and in particular for values between 30 and 60.

Particularly preferred are surfactants of the formula
$R^1O[CH_2CH(CH_3)O]_x[CH_2CH_2O]_yCH_2CH(OH)R^2$ in which $R^1$ stands for a linear or branched aliphatic or aromatic hydrocarbon residue with 4 to 18 carbon atoms or mixtures thereof, $R^2$ denotes a linear or branched hydrocarbon residue with 2 to 26 carbon atoms or mixtures thereof, and x stands for values between 0.5 and 1.5 and y for a value of at least 15.

The group of said nonionic surfactants includes, for example, the $C_{2-26}$ fatty alcohol (PO)$_1$-(EO)$_{15-40}$-2-hydroxyalkyl ethers, particularly also the $C_{8-10}$ fatty alcohol (PO)$_1$-(EO)$_{22}$-2-hydroxydecyl ethers.

Also particularly preferred are closed-terminal-group poly(oxyalkylated) nonionic surfactants of the formula $R^1O[CH_2CH_2O]_x[CH_2CH(R^3)O]_yCH_2CH(OH)R^2$ in which $R^1$ and $R^2$ stand independently of one another for a linear or branched, saturated or mono- or poly-unsaturated hydrocarbon residue with 2 to 26 carbon atoms, $R^3$ is selected independently of one another from —CH$_3$, —CH$_2$CH$_3$, —CH$_2$CH$_2$—CH$_3$, —CH(CH$_3$)$_2$, but preferably stands for —CH$_3$, and x and y stand independently of one another for values between 1 and 32, where surfactants with $R^3$=—CH$_3$ and values for x of 15 to 32 and y of 0.5 and 1.5 are most particularly preferred.

Other preferably used nonionic surfactants are the closed-terminal-group poly(oxyalkylated) surfactants of the formula $R^1O[CH_2CH(R^3)O]_x[CH_2]_kCH(OH)[CH_2]_jOR^2$ in which $R^1$ and $R^2$ stand for linear or branched, saturated or unsaturated, aliphatic or aromatic hydrocarbon residue with 1 to 30 carbon atoms, $R^3$ stands for H or a methyl-, ethyl-, n-propyl-, iso-propyl-, n-butyl-, 2-butyl- or 2-methyl-2-butyl residue, x for values between 1 and 30, k and j for values between 1 and 12, preferably between 1 and 5. If the value x>2, each $R^3$ can be different in the above formula $R^1O[CH_2CH(R^3)O]_x[CH_2]_kCH(OH)[CH_2]_jOR^2$. $R^1$ and $R^2$ are preferably linear or branched, saturated or unsaturated, aliphatic or aromatic hydrocarbon residues with 6 to 22 carbon atoms, wherein residues with 8 to 18 C atoms are particularly preferred. For the $R^3$ residue, H, —CH$_3$ or —CH$_2$CH$_3$ are particularly preferred. Particularly preferred values for x are in the range from 1 to 20, in particular from 6 to 15.

As described above, each $R^3$ can be different in the above formula if x>2. As a result, the alkene oxide unit in the square brackets can be varied. For example, if x stands for 3, the residue $R^3$ can be selected in order to form ethylene oxide ($R^3$=H) or propylene oxide ($R^3$=CH$_3$) units which can be joined together in any sequence, e.g. (EO)(PO)(EO), (EO)(EO)(PO), (EO)(EO)(EO), (PO)(EO)(PO), (PO)(PO)(EO) and (PO)(PO)(PO). The value 3 for x has been selected as an example and can indeed be selected larger, wherein the range of variation increases with increasing x-values and, for example, includes a large number of (EO) groups, combined with a small number of (PO) groups, or vice versa.

Particularly preferred closed-terminal-group poly(oxyalkylated) alcohols of the above formula have values of k=1 and j=1, so that the above formula simplifies to $R^1O[CH_2CH(R^3)O]_xCH_2CH(OH)CH_2OR^2$. In the latter formula, $R^1$, $R^2$ and $R^3$ are as defined above and x stands for numbers from 1 to 30, preferably from 1 to 20 and in particular from 6 to 18. Particularly preferred are surfactants in which the residues $R^1$ and $R^2$ have 9 to 14 C atoms, $R^3$ stands for H and x assumes values of 6 to 15.

Lastly, the nonionic surfactants of the general formula $R^1$—CH(OH)CH$_2$O-(AO)$_w$—$R^2$ have proved to be particularly effective, in which
$R^1$ stands for a straight-chain or branched, saturated or mono- or polyunsaturated $C_{6-24}$ alkyl or alkenyl residue;
$R^2$ stands for a linear or branched hydrocarbon residue with 2 to 26 carbon atoms;
A for stands for a residue from the group CH$_2$CH$_2$, —CH$_2$CH$_2$—CH$_2$, —CH$_2$—CH(CH$_3$), and
w stands for values between 1 and 120, preferably 10 to 80, in particular 20 to 40.

The group of these nonionic surfactants includes, for example, the $C_{4-22}$ fatty alcohol (EO)$_{10-80}$-2-hydroxyalkyl ethers, in particular also the $C_{8-12}$ fatty alcohol (EO)$_{22}$-2-hydroxydecyl ethers and $C_{4-22}$ fatty alcohol (EO)$_{40-80}$-2-hydroxyalkyl ethers.

In different embodiments, the other detergent formulations A, B or other formulations possibly present can also contain one or more of the surfactants described above.

Each of the detergent formulations A, B and C and every other formulation optionally present can contain other usual detergent ingredients, provided they are compatible with the enzyme components or rather surfactant components present.

Examples of such ingredients include builders, but are not limited thereto. The percentage by weight of the builders in the total weight of the detergent formulations is typically 15 to 60 wt %, preferably 20 to 50 wt %.

The group of builders includes, according to the present application, the organic complexing agents as well as the alkali carriers and the anionic polymers.

The group of organic complexing agents includes in particular polycarboxylates/polycarboxylic acids, polymeric carboxylates, aspartic acid, polyacetals, dextrins and other organic cobuilders such as the phosphonates. These families will be described below.

Usable organic complexing agents are, for example, the polycarboxylic acids in the form of the free acid and/or of the sodium salts thereof, wherein polycarboxylic acids are to be understood as meaning carboxylic acids which carry more than one acidic function. These are, for example, citric acid, adipic acid, succinic acid, ethylenediamine disuccinic acid, glutaric acid, malic acid, tartaric acid, maleic acid, fumaric acid, sugar acids, nitrilotriacetic acid (NTA), amino acids (particularly methylglycine diacetic acid (MGDA) or glutamine-N,N-diacetic acid and the salts thereof) and their derivatives as well as mixtures thereof provided such a use is not unacceptable for ecological, toxicological or comparable reasons. In addition to their builder effect, the free acids typically also possess the property of an acidifying component and are therefore also used to set a lower and milder detergent pH value. Particularly to be mentioned here are citric acid, succinic acid, glutaric acid, adipic acid, gluconic acid and any mixtures thereof.

Likewise to be mentioned as other preferred builder substances are polymeric amino dicarboxylic acids, their salts or their precursor substances. Preferred are polyaspartic acids or more specifically their salts. Particularly preferred are methylglycine diacetetic acid (MGDA) or glutamine-N, N-diacetic acid and the salts thereof.

Oxydisuccinates and other derivative of disuccinates, preferably ethylendiamine disuccinate, are other suitable cobuilders. Ethylendiamine-N,N'-disuccinate (EDDS) is preferably used in the form of its sodium or magnesium salts. Also preferred in this context are glycerol disuccinates and glycerol trisuccinates.

Other usable organic complexing agents are, for example, acetylated hydroxycarboxlic acids or rather the salts thereof, which can also be present in lactone form and which contain at least 4 carbon atoms and at least one hydroxyl group as well as up to two acid groups.

With particular preference, at least one of said detergent formulations A, B or C, in particular C, can contain one or more citric acid salts, i.e. citrates, as one of their basic builders. These are preferably present in a proportion of 2 to 40 wt %, in particular 5 to 30 wt %, particularly 7 to 20 wt % referred to the total weight of the individual detergent formulation of 100 wt %.

With particular preference, at least two builders from the aminocarboxylate, carbonate and citrate group are present in at least one of the said detergent formulations A, B or C, particularly in C, wherein the percentage by weight of said builders, referred to the total weight of the detergent formulation, is preferably 5 to 60 wt %, preferably 15 to 50 wt % and in particular 25 to 40 wt %. In particular, MGDA and/or GLDA or rather their respective salts are preferably used as aminocarboxylates. Here the total amount of aminocarboxylate(s) present in the respective detergent formulation, particularly in detergent formulation C, is preferably 2 to 40 wt %, in particular 5 to 30 wt %, especially 7 to 20 wt % referred to the total weight of the respective detergent formulation. The combination of two or more builders from the above mentioned group has been found to be advantageous for the washing and rinsing performance of automatic dishwashing agents according to the invention.

The complex-forming phosphonates constitute a group of other organic complexing agents that can be used in the detergent formulations according to the invention, said group comprising, in addition to 1-hydroxyethane-1,1-diphosphonic acid, a number of different compounds such as diethylentriamine penta(methylene phosphonic acid) (DTPMP). Preferred are in particular hydroxyalkane or aminoalkane phosphonates. Among the hydroxyalkane phosphonates, 1-hydroxyethane-1,1-diphosphonate (HEDP) is of particular importance as a cobuilder. It is preferably used as a sodium salt, wherein the disodium salt reacts neutral and the tetrasodium salt alkaline (pH 9). Possible aminoalkane phosphonates are preferably ethylenediaminetetramethylene phosphonate (EDTMP), diethylenetriaminepentamethylene phosphonate (DTPMP) and the higher homologs thereof. They are preferably used in the form of neutral reacting sodium salts, e.g. as a hexasodium salt of EDTMP or as a hepta- and octasodium salt of DTPMP. Of the phosphonate class, HEDP is the preferred builder. The aminoalkane phosphonates additionally possess a pronounced heavy metal binding capability. Accordingly, it may be preferable, particularly if the agents also contain bleaches, to use aminoalkane phosphonates, particularly DTPMP, or mixtures of the phosphonates mentioned.

A second builder group is constituted by the alkali carriers. The alkali carrier group includes the carbonates and/or hydrogencarbonates as well as the alkali hydroxides. Within the frame of reference of this application, the carbonate and hydrogencarbonate group is subsumed under the term (hydrogen)carbonate.

To increase or set the alkalinity, the detergent formulations can contain alkali hydroxide(s).

The detergent formulations according to the invention can contain other builders in addition to the builders described above. An example of corresponding builders are the phosphates which can preferably be used in the detergent formulations in the form of alkali metal phosphates, with pentasodium or pentapotassium phosphate (sodium or potassium tripolyphosphate) being particularly preferred.

However, inventively preferred detergent formulations contain less than 10 wt %, with particular preference less than 5 wt % and in particular less than 2 wt % phosphate. Phosphate-free detergent formulations are most particularly preferred according to the invention. Also preferred are detergent formulations according to the invention that contain less than 2 wt %, preferably less than 1 wt % and in particular less than 0.5 wt % silicate. Reducing the phosphate content and reducing the silicate content have both been found to be advantageous for stability.

The anionic polymers with cleaning action constitute a third group of builders present in the detergent formulations described here.

The anionic polymers with cleaning action can have two, three, four or more different monomer units. The group of said polymers also comprises, among other things, in addition to the homo- and copolymeric polycarboxylates, the copolymeric polysulfonates which, in addition to monomers from the unsaturated carboxylic acid group, have at least one other monomer from the unsaturated sulfonic acid group.

The polymeric polycarboxylates constitute a first group of anionic polymers with cleaning action. Examples of such polymers are the alkali salts of polyacrylic acid or of polymethacrylic acid, e.g. those having a relative molecular mass of 500 to 70000 g/mol.

Suitable anionic polymers are in particular polyacrylates preferably having a molecular mass of 2000 to 20000 g/mol. Because of their superior solubility, from this group the short-chain polyacrylates having molecular masses of 2000 to 10000 g/mol, and with particular preference of 3000 to 5000 g/mol, may again be preferred.

Also suitable are copolymeric polycarboxylates, particularly those of acrylic acid with methacrylic acid and of acrylic acid or methacrylic acid with maleic acid. Copolymers of acrylic acid with maleic acid containing 50 to 90 wt % acrylic acid and 50 to 10 wt % maleic acid have been found to be particularly suitable. Their relative molecular mass, referred to free acids, is in general 2000 to 70000 g/mol, preferably 20000 to 50000 g/mol and in particular 30000 to 40000 g/mol.

Preferred copolymeric polysulfonates contain, in addition to sulfonic-group-containing monomer(s) at least one monomer from the group of unsaturated carboxylic acids.

Used with particular preference as unsaturated carboxylic acid(s) is/are unsaturated carboxylic acids of the formula $R^1(R^2)C=C(R^3)COOH$ in which $R^1$ to $R^3$, independently of one another, stands for —H, —CH$_3$, a straight-chain or branched saturated alkyl residue with 2 to 12 carbon atoms, a straight-chain or branched, mono- or polyunsaturated alkenyl residue with 2 to 12 carbon atoms, with —NH$_2$, —OH or —COOH substituted alkyl or alkenyl residues as defined above, or for —COOH or —COOR$^4$, wherein R$^4$ is a saturated or unsaturated, straight-chain or branched hydrocarbon residue with 1 to 12 carbon atoms.

Particularly preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic acid anhydride, fumaric acid, itaconic acid, citraconic acid, methylenemalonic acid, sorbic acid, cinnamic acid or mixtures thereof. The unsaturated dicarboxylic acids can self-evidently also be used.

In the case of the monomers containing sulfonic acid groups, those of the formula

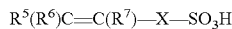
$R^5(R^6)C=C(R^7)-X-SO_3H$ are preferred, in which R$^5$ to R$^7$, independently of one another, stands for —H, —CH$_3$, a straight-chain or branched saturated alkyl residue with 2 to 12 carbon atoms, a straight-chain or branched, mono- or polyunsaturated alkenyl residue with 2 to 12 carbon atoms, with —NH$_2$, —OH or —COOH substituted alkyl or alkenyl residues, or for —COOH or —COOR$^4$, wherein R$^4$ is a saturated or unsaturated, straight-chain or branched hydrocarbon residue with 1 to 12 carbon atoms, and X stands for an optionally present spacer group which is selected from —(CH$_2$)$_n$— with n=0 to 4, —COO—(CH$_2$)$_k$— with k=1 to 6, —C(O)—NH—C(CH$_3$)$_2$—, —C(O)—NH—C(CH$_3$)$_2$—CH$_2$— and —C(O)—NH—CH(CH$_2$CH$_3$)—.

Preferred among these monomers are those having the formula

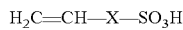
$H_2C=CH-X-SO_3H$

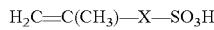
$H_2C=C(CH_3)-X-SO_3H$

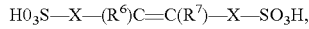
$HO_3S-X-(R^6)C=C(R^7)-X-SO_3H$, in which R$^6$ and R$^7$ are selected independently of one another from —H, —CH$_3$, —CH$_2$CH$_3$, —CH$_2$CH$_2$CH$_3$, —CH(CH$_3$)$_2$ and X stands for an optionally present spacer group which is selected from —(CH$_2$)$_n$— with n=0 to 4, —COO—(CH$_2$)$_k$— with k=1 to 6, —C(O)—NH—C(CH$_3$)$_2$—, —C(O)—NH—C(CH$_3$)$_2$—CH$_2$— and —C(0)—NH—CH(CH$_2$CH$_3$)—.

Particularly preferred monomers containing sulfonic acid groups are 1-acrylamido-1-propane sulfonic acid, 2-acrylamido-2-propane sulfonic acid, 2-acrylamido-2-methyl-1-propane sulfonic acid, 2-methacrylamido-2-methyl-1-propane sulfonic acid, 3-methacrylamido-2-hydroxy-propane sulfonic acid, allyl sulfonic acid, methallyl sulfonic acid, allyloxybenzene sulfonic acid, methallyloxybenzene sulfonic acid, 2-hydroxy-3-(2-propenyloxy)propane sulfonic acid, 2-methyl-2-propene-1-sulfonic acid, styrene sulfonic acid, vinyl sulfonic acid, 3-sulfopropyl acrylate, 3-sulfopropyl methacrylate, sulfomethacrylamide, sulfomethylmethacrylamide and mixtures of said acids or water-soluble salts thereof.

The sulfonic acid groups can be present wholly or partially in neutralized form in the polymers, i.e. the acidic hydrogen atom of the sulfonic acid group can be exchanged for metallic ions, preferably alkali metallic ions and in particular for sodium ions, in some or all of the sulfonic acid groups. The use of partially or fully neutralized copolymers containing sulfonic acid groups is preferred according to the invention.

In another preferred embodiment, in addition to monomers containing carboxyl groups and sulfonic acid groups, the copolymers also comprise at least one nonionic, preferably hydrophobic monomer.

Preferably used as nonionic monomers are monomers of the general formula $R^1(R^2)C=C(R^3)-X-R^4$ in which $R^1$ to $R^3$ stands independently of one another for —H, —CH$_3$ or —C$_2$H$_5$, X stands for an optionally present spacer group which is selected from —CH$_2$—, —C(O)O— and —C(O)—NH—, and R$^4$ stands for a straight-chain or branched saturated alkyl residue with 2 to 22 carbon atoms or for an unsaturated, preferably aromatic residue with 6 to 22 carbon atoms.

Particularly preferred nonionic monomers are butene, isobutene, pentene, 3-methylbutene, 2-methylbutene, cyclopentene, hexene, hexene-1, 2-methlypentene-1, 3-methlypentene-1, cyclohexene, methylcyclopentene, cycloheptene, methylcyclohexene, 2,4,4-trimethylpentene-1, 2,4,4-trimethylpentene-2, 2,3-dimethylhexene-1, 2,4-diemthylhexene-1, 2,5-dimethlyhexene-1, 3,5-dimethylhexene-1, 4,4-dimehtylhexane-1, ethylcyclohexyne, 1-octene, α-olefins with 10 or more carbon atoms such as, for example, 1-decene, 1-dodecene, 1-hexadecene, 1-octadecene and C22-α-olefin, 2-styrene, α-methylstyrene, 3-methylstyrene, 4-propylstyrene, 4-cyclohexylstyrene, 4-dodecylstyrene, 2-ethyl-4-benzylstyrene, 1-vinylnaphthalene, 2-vinylnaphthalene, acrylic acid methyl ester, acrylic acid ethyl ester, acrylic acid propyl ester, acrylic acid butyl ester, acrylic acid pentyl ester, acrylic acid hexyl ester, methacrylic acid methyl ester, N-(methyl)acrylamide, acrylic acid-2-ethylhexyl ester, methacrylic acid-2-ethylhexyl ester, N-(2-ethylhexyl)acrylamide, acrylic acid octyl ester, methacrylic acid octyl ester, N-(octyl)acrylamide, acrylic acid lauryl ester, methacrylic acid lauryl ester, N-(lauryl)acrylamide, acrylic acid stearyl ester, methacrylic acid stearyl ester, N-(stearyl)acrylamide, acrylic acid behenyl ester, methacrylic acid behenyl ester and N-(behenyl)acrylamide or mixtures thereof.

The detergent formulations, particularly those containing no enzyme components, can also contain at least one oxygen bleaching agent as an ingredient. Of particular importance among the compounds acting as bleaching agents yielding H$_2$O$_2$ in water are sodium percarbonate, sodium perborate tetrahydrate and sodium perborate monohydrate. Other suitable bleaching agents are peroxypyrophosphates, citrate perhydrates and H$_2$O$_2$ yielding peroxy acid salts or peroxy acids, such as perbenzoates, peroxophthalates, diperazelaic acid, phthaloiminoperoxy acid or diperdodecanedioic acid. Bleaching agents from the group of organic bleaching agents can also be used. Typical organic bleaching agents are the diacyl peroxides such as dibenzoyl peroxide, for example. Other typical organic bleaching agents are the peroxy acids, notable examples being in particular the alkyl peroxy acids and the aryl peroxy acids.

With particular preference, hydrogen peroxide is used as an oxygen bleaching agent. A detergent formulation containing an oxygen bleaching can be stabilized by adding tin compounds, phosphonates or radical traps.

Another constituent of the detergent formulations that can be used according to the invention is an organic solvent.

Preferred organic solvents come from the group of mono- or polyvalent alcohols, alkanolamines or glycol ethers. The solvents are preferably selected from ethanol, n- or i-propanol, butanol, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol methyl or ethyl ether, methoxy, ethoxy or butoxy triglycol, 1-butoxyethoxy-2-propanol, 3-methyl-3-methoxybutanol, propylene glycol t-butyl ether and mixtures of these solvents. The percentage by weight of these organic solvents in the total weight of the detergent formulations is preferably 5 to 80 wt %, especially 8 to 60 wt % and in particular 10 to 50 wt %.

In addition to the constituents described above such as enzymes, nonionic surfactants from the group of hydroxy mixed ethers, solvents, builders and bleaching agents, the detergent formulations can contain other ingredients, e.g. active substances from the group of detergent-action polymers, corrosion inhibitors, fragrances or dyes.

The detergent product format can be characterized in that the detergent formulations A, B and C are provided separately from one another in a common cartridge.

The detergent formulations A, B and C described above differ in respect of their composition, i.e. are not identical.

The above described combination of detergents is packaged in the form of separate accommodation compartments, wherein each of said compartments contains one of the inter-combined detergents. Examples of such packaging formats are cartridges having two, three, four or more compartments separated from one another, e.g. double, triple, quadruple or multi-compartment bottles. By separating the detergents of different composition, undesirable reactions caused by chemical incompatibility can be eliminated.

The detergent formulations according to the invention are preferably dispensed by means of a special dosing system. In a preferred embodiment, the above described cartridges of the detergent product formats are provided with a dosing device that is detachable from the cartridge. Such a dosing device can be connected to the cartridge by means of an adhesive, latching, snap-on or plug-in connection. The separation of the cartridge and dosing device makes it easier to fill the cartridge, for example. Alternatively, the detachability of the cartridge and dosing device enables the cartridges to be replaced on the dosing device. Such a replacement can be indicated e.g. when the wash program is changed or when the cartridge is completely empty.

Such a detergent dosing system can include the detergent formulations described above, as well as a cartridge for the detergent formulations in which the detergent formulations are present in separate accommodation compartments; and a dosing device connected or connectable to the cartridge. The cartridge and the dosing device are preferably detachably connected to one another, but can also be non-detachably connected to one another.

In a preferred embodiment, the above mentioned detergent dosing systems, comprising detergent formulations according to the invention, a cartridge and a dosing device detachably or non-detachably connected to the cartridge, are provided in a common outer packaging, wherein with particular preference the filled cartridge and the dosing device are contained separately from one another in the outer packaging. The outer packaging is used for the storage, transportation and presentation of the detergent product format and protects it from contamination, shock and impact. Particularly for presentation purposes, the outer packaging should be of at least partially transparent design.

Alternatively or in addition to an outer packaging, the detergent product format can be marketed in conjunction with a water-conducting household appliance such as a dishwasher, for example. Such a combination is advantageous particularly in cases where the course of the automatic dishwashing process (e.g. duration, temperature profile, water feed) and the detergent recipe or the control electronics of the dosing device are matched to one another.

The basic elements of the dosing system are a detergent product format and dosing device which can be linked to the cartridge and which is in turn made up of other modules such as a circuit board, actuator, locking element, sensor, power source and/or control unit, for example.

It is preferred that the dosing system is movable. Movable in the context of this application means that the dosing system is not non-detachably connected to a water-conducting device such as a dishwasher, washing machine, tumble dryer or similar, but can be removed by the user e.g. from a dishwasher or can be positioned, i.e. manipulated independently, in a dishwasher.

According to an alternative embodiment, it is also conceivable that the dosing device is not user-detachably connected to a water-conducting device such as a dishwasher, washing machine, tumble dryer or similar, and that only the cartridge is movable.

In the context of this application, a cartridge is to be understood as meaning a packaging means that is suitable for encasing or holding together flowable or scatterable formulations and which can be linked to a dosing device for dispensing the formulation.

In particular, a cartridge can also comprise a plurality of compartments which can be filled with different compositions. It is also conceivable for a plurality of containers to be arranged to form a cartridge unit.

In another embodiment, the cartridge is of one-piece design. This means that cartridges can be produced inexpensively in one manufacturing step, in particular by suitable blow molding processes. The compartments of a cartridge can be separated from one another e.g. by ribs or integral bridges. The cartridge can also be of multi-piece design comprising elements produced by injection molding and then fitted together. It is also conceivable for the cartridge to be of multi-piece design such that at least one compartment, preferably all the compartments, can be individually removed from or inserted in the dosing device. In the event of a different degree of use of a formulation from one compartment, this makes it possible to replace an already empty compartment while the other compartments, which may still contain formulation, remain in the dosing device. Selective topping-up of the compartments with their respective formulations can thus be achieved on an as-required basis.

The compartments of a cartridge can be fixed to one another by suitable joining methods so that a container unit is formed. The compartments can be detachably or non-detachably fixed to one another by a suitable form fit, force fit or material bond. In particular, the fixing can take the form of one or more of the types of connection from the group of snap-ins, hook and loop fastenings, press fits, fusion bonds, adhesive bonds, welded joints, soldered joints, screwed connections, keyed joints, clamped or bounce connections. In particular, the fixing can also be implemented by a shrink-on sleeve which, in a heated state, is pulled over the entire cartridge or sections thereof and encloses the compartments or cartridge in the cooled state.

In order to ensure that the compartments are emptied completely, the floors of the compartments can be made to funnel into the discharge holes. In addition, by suitable material selection and/or surface finish, the inner wall of a compartment can be designed such that little of the formulation adheres to the compartment wall. This measure also provides a means of optimizing still further the ability to completely empty a compartment.

The compartments of a cartridge can have the same or different capacities. In the case of a two-compartment configuration, the ratio of the container volumes is preferably 5:1, in the case of a three-compartment configuration preferably 5:1:1, these configurations being particularly suitable for use in dishwashers.

The cartridge usually has a capacity of <5000 ml, in particular <2000 ml, preferably between 10 and 1500 ml, with preference between 50 and 900 ml, and in particular between 250 and 800 ml.

The cartridge can have any physical shape. It can be, for example, cubical, spherical or plate-like.

Commercially available dishwashers are usually designed such that provision is made for stacking larger items such as pans or large plates in the lower basket of the dishwasher. In order to prevent less than optimum positioning of the dosing system in the upper basket by the user, in an advantageous embodiment of the invention the dosing system is dimensioned such that the dosing system can only be placed in the holders provided for that purpose in the lower basket. To this end, the width and height of the dosing system can be selected in particular between 150 and 300 mm, with particular preference between 175 and 250 mm.

However, it is also conceivable for the dosing unit to be of cup-shaped design, having an essentially circular or square base area.

The control unit, sensor unit and at least one actuator which are necessary for operation are incorporated in the dosing device. A power source is preferably likewise disposed in the dosing device.

The dosing device preferably consists of a splash-protected housing which prevents splash water, as may occur when it is used in a dishwasher, for example, from getting inside the dosing device.

It is particularly preferred that the dosing device has at least one first interface which, in or on a water-conducting appliance such as in particular a water-conducting household appliance, preferably a dishwasher or a washing machine, interacts with a corresponding interface implemented so as to bring about transmission of electrical energy from the water-conducting appliance to the dosing device.

In one embodiment of the invention, the interfaces are implemented by plug-in connectors. In another embodiment, the interfaces can be implemented so as to provide wireless transmission of electrical energy.

In an advantageous further development of the invention, a second interface is implemented on the dosing device and on the water-conducting appliance such as a dishwasher, for example, for transmitting electromagnetic signals which in particular represent operating state, measurement and/or control information of the dosing device and/or of the water-conducting appliance such as a dishwasher.

By means of an adapter, simple attachment of the dosing system to a water-conducting household appliance can be implemented. The adapter is used to mechanically and/or electrically connect the dosing system to the water-conducting household appliance.

The adapter is connected, preferably in a fixed manner, to a water-carrying line of the household appliance. However, it is also conceivable for the adapter to be designed for positioning in or on the household appliance in which the adapter is hit by the water flow and/or spray jet of the household appliance.

The adapter makes it possible to implement a dosing system both for a standalone and a built-in version. It is also possible to implement the adapter as a kind of charging station for the dosing system in which, for example, the power source of the dosing device is charged or data is exchanged between the dosing device and the adapter.

The adapter can be disposed in a dishwasher on one of the inner walls of the wash tub, particularly on the inside of the dishwasher door. However, it is also possible for the adapter as such to be positioned inaccessibly for the user in the water-conducting household appliance, so that the dosing device is inserted into the adapter e.g. during assembly of the household appliance, wherein the adapter, the dosing device and the household appliance are implemented such that a cartridge can be connected to the dosing device by the user.

The detergent product formats described are suitable for dispensing by means of a dosing system located inside a dishwasher. Such a dosing system, which can be immovably incorporated into the interior the dishwasher (machine-integrated dosing device) but can self-evidently also be inserted into the interior as a movable device (standalone dosing device), contains multiples of the amount of detergent required for carrying out an automatic wash.

Movable in the context of this application means that the dispensing and dosing system is not non-detachably connected to a device such as, for example, a dishwasher, washing machine, tumble dryer or similar, but can be removed from a dishwasher or positioned in a dishwasher, for example.

To summarize, both the detergent combinations and the detergent product formats as refill packs are suitable for dosing devices immovably incorporated in the interior of a dishwasher and for movable dosing devices designed for positioning in the interior of a dishwasher.

Another aspect of the invention relates to the use of a herein described detergent product format or of a herein described detergent dosing system as a detergent reservoir for a water-conducting household appliance. Said dosing system can be i) a dosing device immovably incorporated in the interior of a water-conducting household appliances or ii) a movable dosing device designed to be positioned in the interior of a water-conducting household appliance.

Also proposed is a computer program product which causes at least one step of the method as explained above to be carried out on a program-controlled device.

A computer program product, such as a computer program means, can be provided or supplied, for example, as a storage medium such as e.g. a memory card, USB stick, CD-ROM, DVD, or also in the form of a downloadable file from a server in a network. This can take place, for example, in a wireless communication network by the transmission of a corresponding file containing the computer program product or the computer program means.

Other possible implementations of the invention also include not explicitly stated combinations of features or embodiments described above or in the following in respect of the exemplary embodiments given. The person skilled in the art will also add individual aspects as improvements or supplementations to the respective basic form of the invention.

BRIEF DESCRIPTION OF THE DRAWINGS

Other advantageous embodiments and aspects of the invention are set forth in the sub-claims and in the examples described below. The invention will now be explained in greater detail on the basis of preferred embodiments with reference to the accompanying drawings in which:

DETAILED DESCRIPTION OF EXEMPLARY EMBODIMENTS OF THE PRESENT INVENTION

Figure 1:
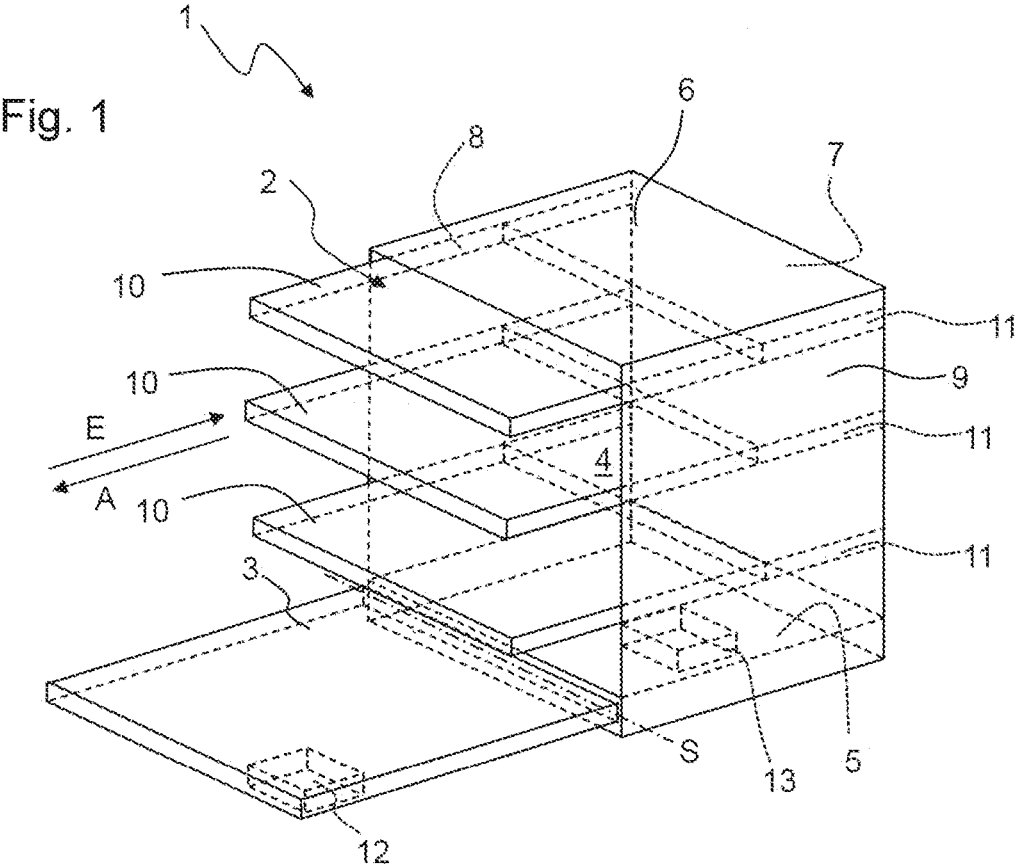
FIG. 1 shows a perspective view of an embodiment of a water-conducting household appliance.

Unless otherwise stated, identical or functionally identical elements are provided with the same reference characters in the figures.

FIG. 1 shows a perspective view of a first embodiment of a water-conducting household appliance 1, in particular a dishwasher or a washing machine. In the following, a dishwasher will be described by way of example. The elements and functions described apply similarly to a washing machine where applicable.

The dishwasher 1 has a carcass enclosing a wash tub 2, and a door 3. The wash tub 2 and the door 3 form a washing chamber 4 for cleaning wash items. In FIG. 1 the door 3 is shown in the open position. The door 3 can be closed or opened by swiveling it about a swivel axis S provided at the bottom of the door 3.

The wash tub 2 is cuboidal, for example, and can have a floor 5, a ceiling 6 opposite the floor 5, a rear wall 7 opposite the door 3, and side walls 8, 9 opposite one another. In particular the sidewalls 8, 9 can be made of stainless steel sheeting.

The dishwasher 1 also has at least one loading level 10. The at least one loading level 10 is preferably a wash item holder of the dishwasher 1. In particular a plurality of loading levels 10 can be provided which can comprise a lower basket, an upper basket and/or a cutlery drawer. The plurality of loading levels 10 are preferably disposed one above the other in the wash tub 2. Each loading level 10 is optionally displaceable in an insertion direction E into the wash tub 2 or in a withdrawal direction A therefrom. For this purpose a rail 11 is preferably provided on both sides of the respective loading level 10.

A control device 12 optionally provided in the carcass or in the door 3 of the dishwasher 1 is designed to control the running of wash programs for cleaning wash items. The control device 12 can have a device 12 for determining a soiling of the wash items, as described, for example, in FIG. 2.

Also shown is a sensor 13 which can be inserted at different locations in the dishwasher 1. The sensor 13 is used to carry out near-infrared spectroscopy in order to detect organic compounds in the wash water of the dishwasher 1.

The control device 12 is designed to operate the sensor 13 and possibly a number of other sensors and/or actuators of the household appliance 1.

Figure 2:
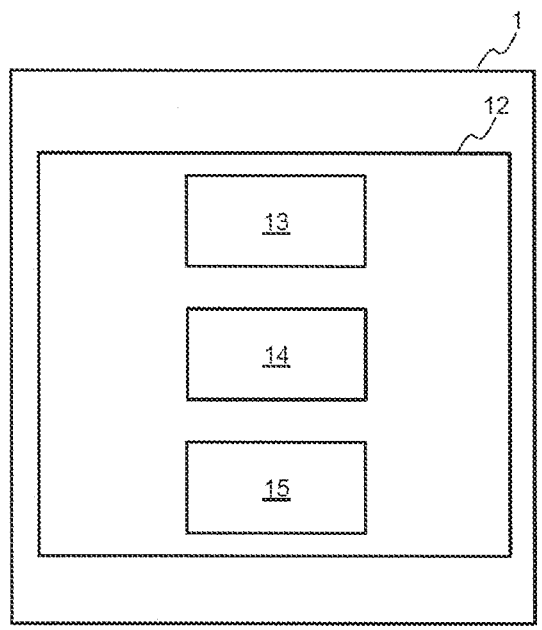
FIG. 2 shows a schematic block diagram of an embodiment of a device for determining a soiling of wash items in the water-conducting household appliance.

FIG. 2 shows a schematic block diagram of an embodiment of a device 12 for determining a soiling of wash items in the water-conducting household appliance, e.g. a dishwasher 1.

The device 12 has a sensor 13, a determination unit 14 and an adjustment unit 15.

The sensor 13 performs near-infrared spectroscopy, hereinafter referred to as NIR measurement, in order to measure organic compounds in the wash water of the dishwasher 1. Based on the organic compounds measured, the determination unit 14 can determine a soiling of the wash items.

The adjustment unit 15 can use the information about the soiling to adjust wash parameters of a current wash program, or adjust stored wash programs already present. For this purpose the adjustment unit 15 can also adjust automatic dosing by a dosing unit 22.

The sensor 13 can be disposed at different locations in the dishwasher 1 as will now be described with reference to FIGS. 3 to 7.

Figure 3:
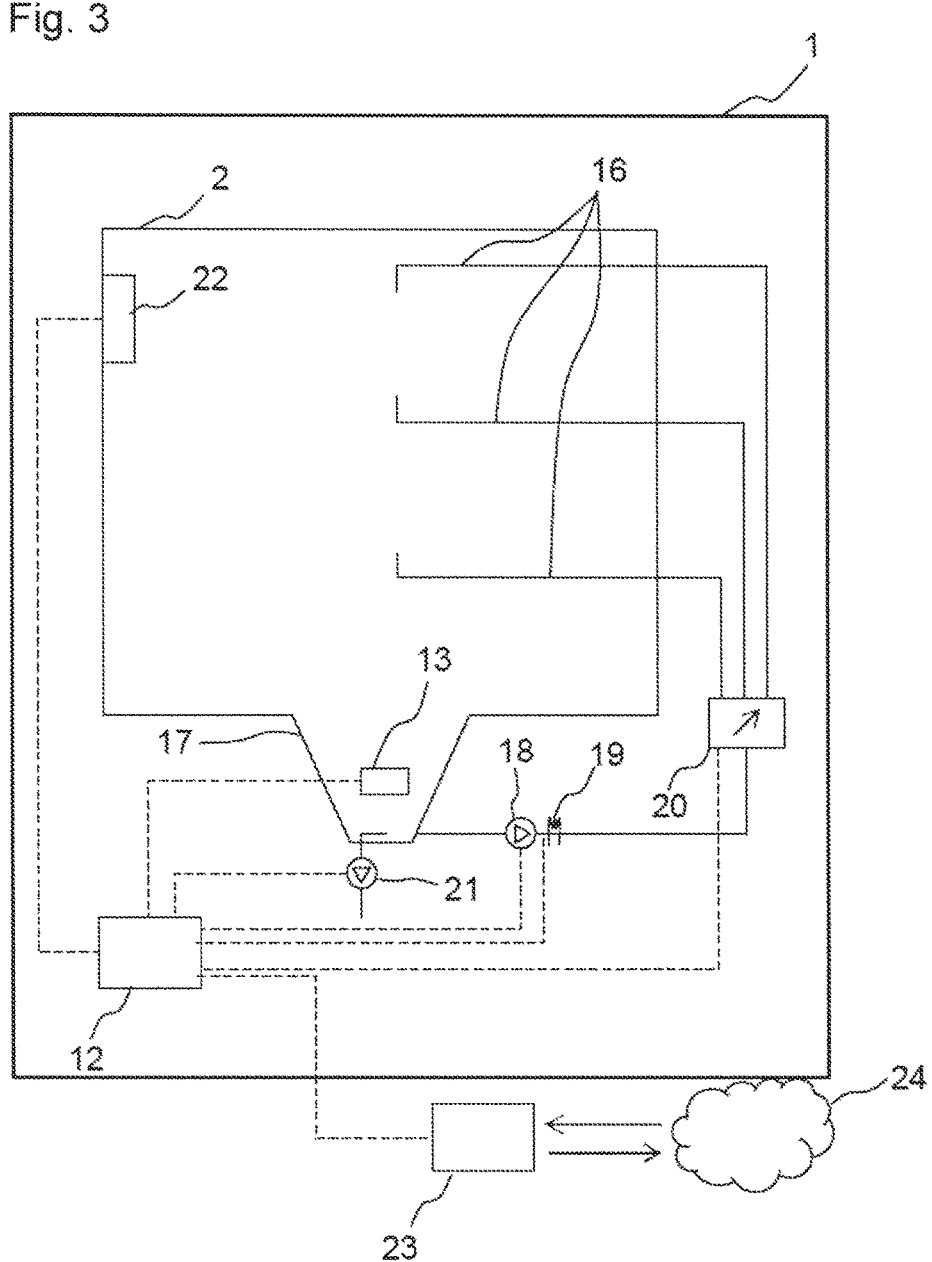
FIG. 3 shows a first arrangement of the device for determining a soiling of wash items in the wash tub of the water-conducting household appliance.

FIG. 3 shows a first arrangement of the device 12 for determining a soiling of wash items in the wash tub 2 of the dishwasher 1.

In this arrangement the sensor 13 is located in the pump sump 17 below the different spray levels 16. This results in a high measurement accuracy, as this is a somewhat low-turbulence region. The control device or device 12 for determining the soiling acquires the data from the sensor 13 (selectively or permanently) and compares it against a stored calibration model and then with predetermined threshold values. Decisions for the ongoing program are taken on the basis of the predefined logic. The following units can be controlled: the circulating pump 18, the heating unit 19 for the circulating pump 18, the water switch 20, the drain pump 21 or the dosing unit 22 for powder, mono- and/or multi-function tabs, rinse aids and/or individual components of a detergent system. The device 12 can also be connected via an Internet communication unit 23 to a database on external server 24.

Figure 4:
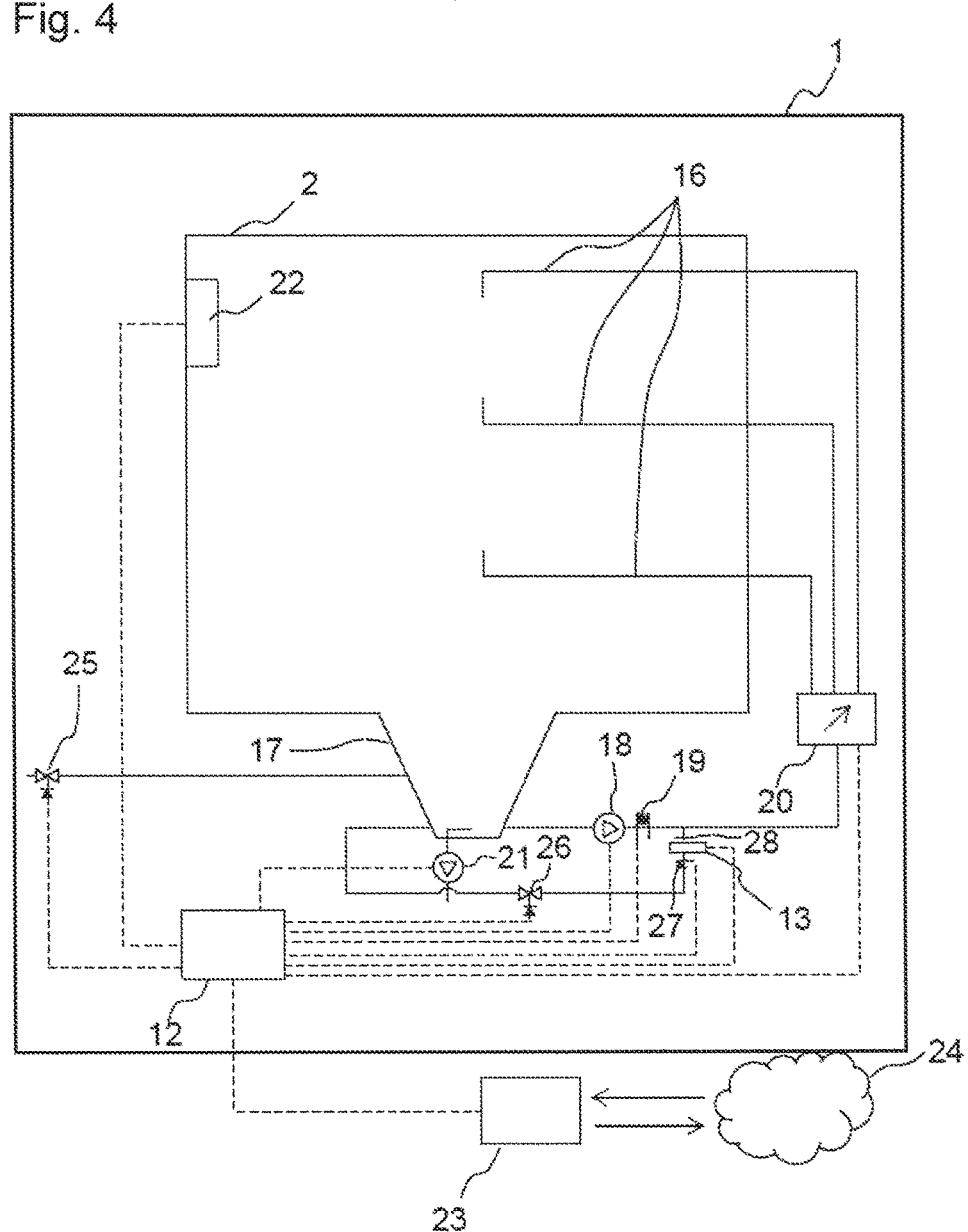
FIG. 4 shows a second arrangement of the device for determining a soiling of wash items in the wash tub of the water-conducting household appliance.

FIG. 4 shows a second arrangement of the device 12 for determining the soiling of wash items in the wash tub 2 of the dishwasher 1.

In this arrangement the sensor 13 is located in a bypass downstream of the circulating pump 18 and the wash water is fed through the sensor 13 and back into the tub 2 or pump sump 17 (e.g. below the sieve system). The bypass can optionally be "shut off" and opened via a valve 26. The wash liquor is in the quiescent state, i.e. there is no flow of any kind.

The mounting of the sensor 13 can be selected such that solid particles can settle to the bottom when the valve 26 is closed, i.e. without flow movement. A heating and/or cooling device 27 can additionally be installed in the measuring section. Solids can also be filtered out via a filter 28 so that they do not affect a measurement. Under normal flow conditions the filter 28 can be cleaned in the direction of the water switch 20. In addition, in this arrangement the device 12 can control the fresh water 25.

Figure 5:
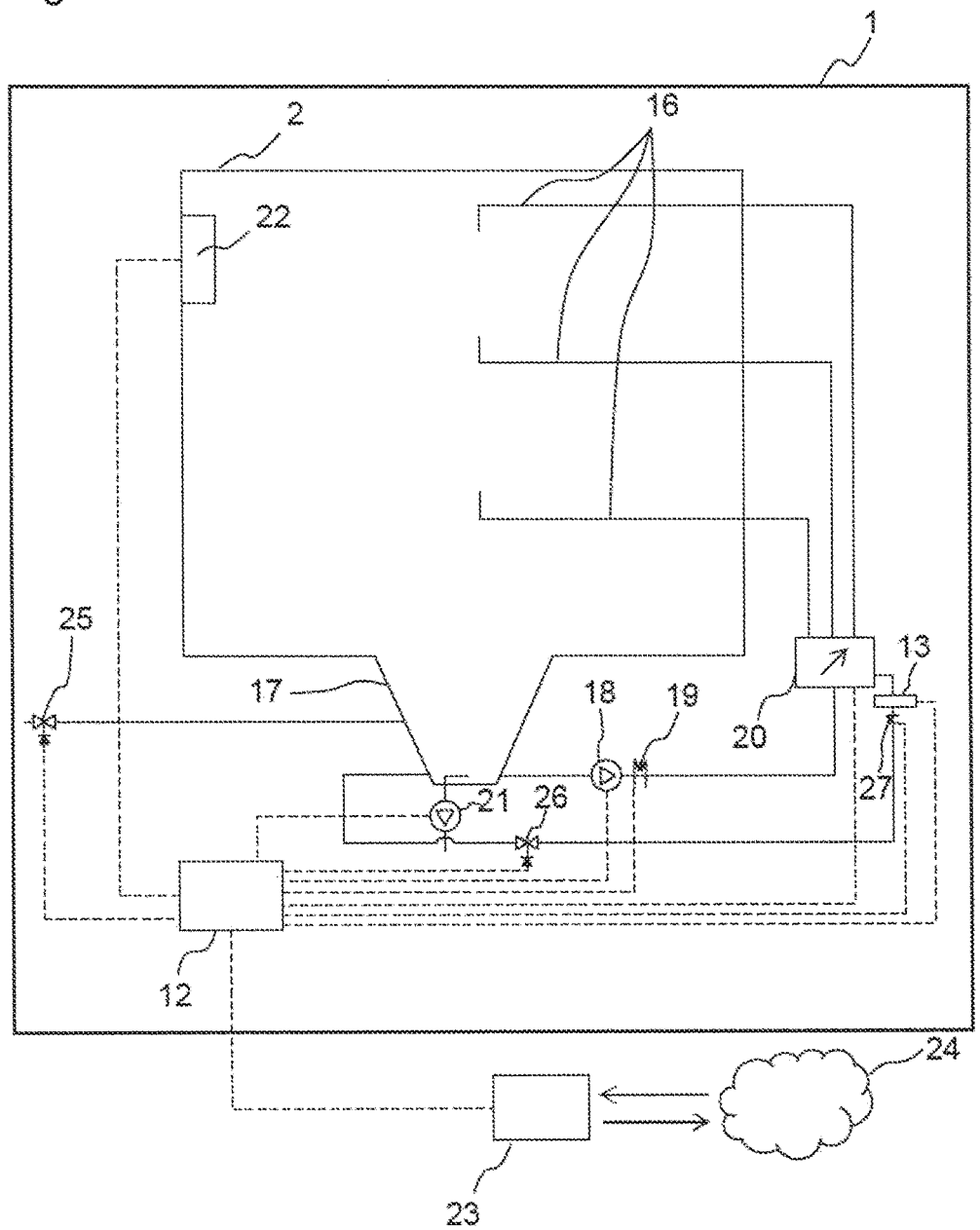
FIG. 5 shows a third arrangement of the device for determining a soiling of wash items in the wash tub of the water-conducting household appliances.

FIG. 5 shows a third arrangement of the device 12 for determining the soiling of wash items in the wash tub 2 of the dishwasher 1.

As in the case of the arrangement in FIG. 4, the sensor 13 is located in a bypass. Here, however, the port for the liquor reservoir at the water switch 20 is used.

Figure 6:
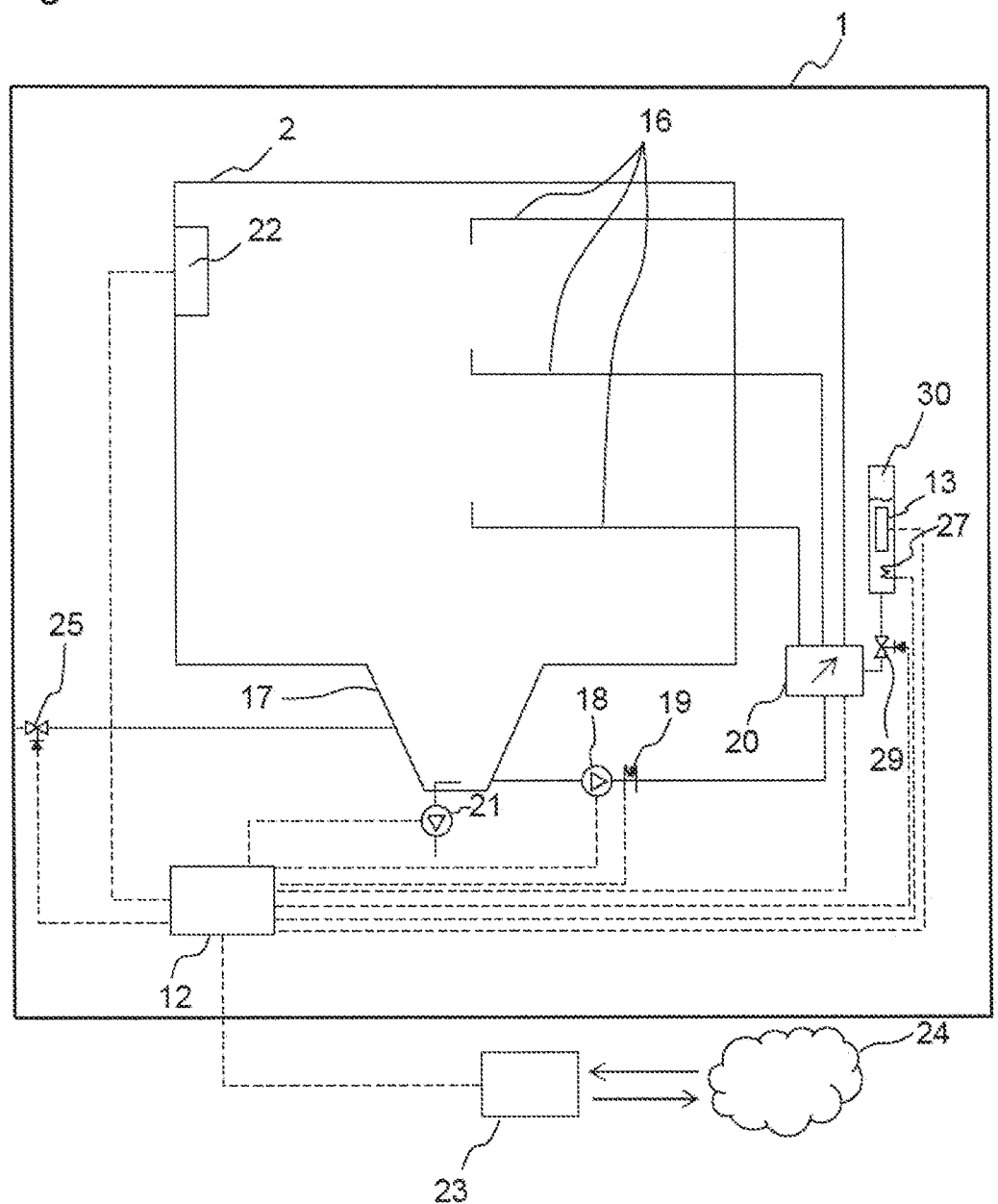
FIG. 6 shows a fourth arrangement of the device for determining a soiling of wash items in the wash tub of the water-conducting household appliances.

FIG. 6 shows a fourth arrangement of the device 12 for determining the soiling of wash items in the wash tub 2 of the dishwasher 1.

In the case of the arrangement in FIG. 6, the sensor 13 is accommodated in a measurement housing 30 having an upstream valve 29. The wash liquor can therefore be present in flow-stabilized form and additionally heated or cooled via a unit 27.

Figure 7:
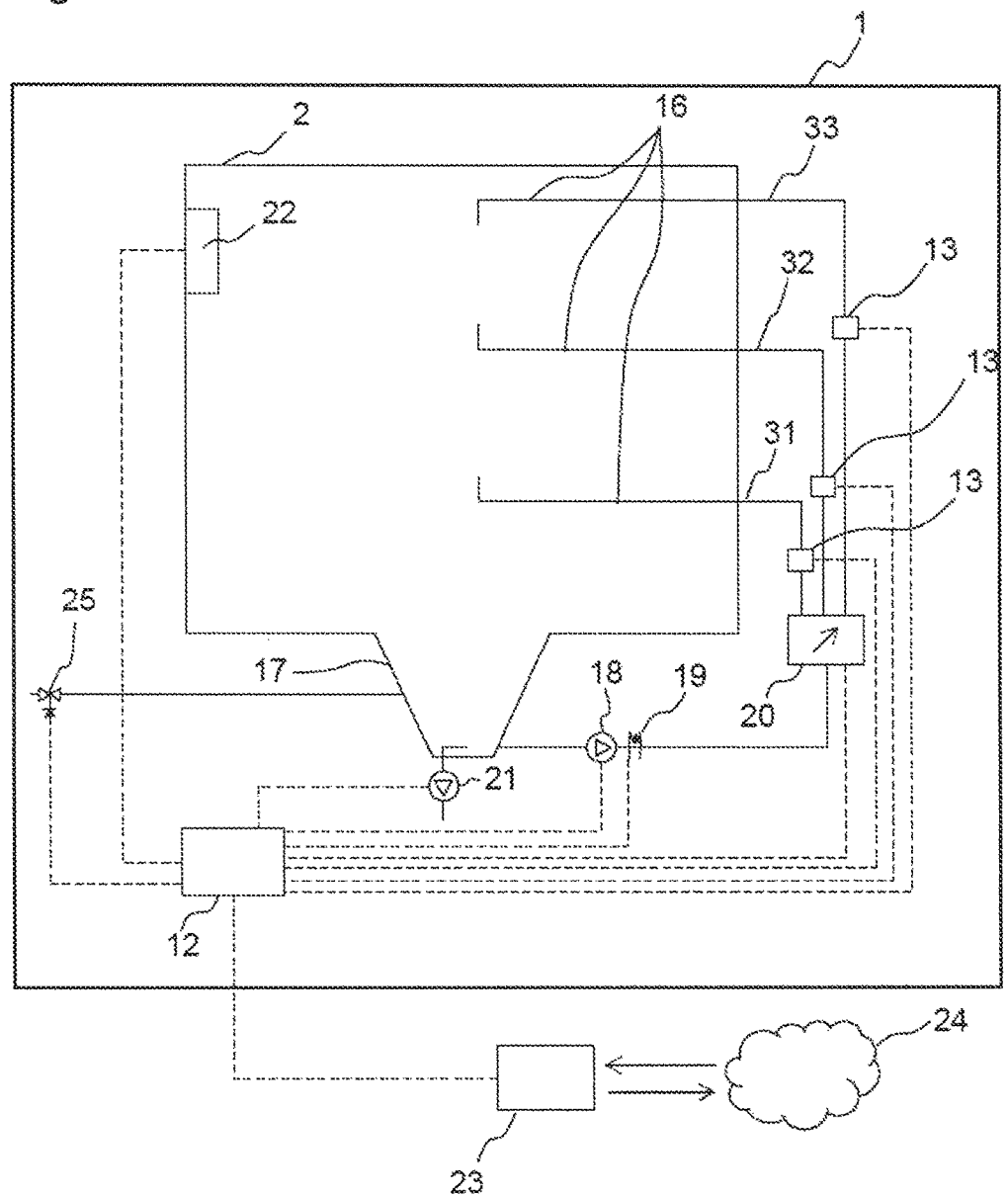
FIG. 7 shows a fifth arrangement of the device for determining a soiling of wash items in the wash tub of the water-conducting household appliances.

FIG. 7 shows a fifth arrangement of the device 12 for determining the soiling of wash items in the wash tub 2 of the dishwasher 1.

In this arrangement a plurality of sensors 13 are positioned in the feed lines 31, 32, 33 of the different spray levels 16.

Figure 8:
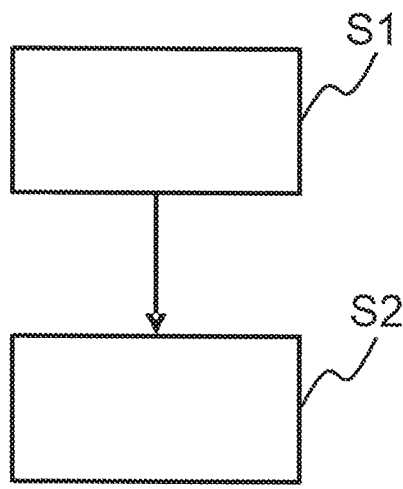
FIG. 8 shows an exemplary embodiment of a method for determining a soiling of wash items in the water-conducting household appliance.

FIG. 8 shows an exemplary embodiment of a method for determining a soiling of wash items in the water-conducting household appliance 1.

In step S1, organic compounds in the wash water of the water-conducting household appliance 1 are measured using near-infrared spectroscopy.

In step S2, the soiling of the wash items is determined on the basis of the organic compounds measured.

Figure 9:
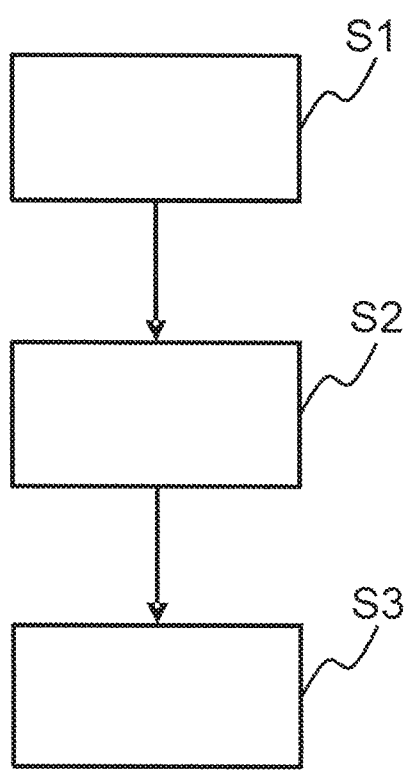
FIG. 9 shows an exemplary embodiment of a method for washing dishes or fabrics in a water-conducting household appliance.

FIG. 9 shows an exemplary embodiment of a method for washing dishes or fabrics in a water-conducting household appliance 1, in particular in a dishwasher or in a washing machine.

In step S1, spectral measured values of dirt components in a rinsing or detergent solution in the water-conducting household appliance 1 are acquired using near-infrared spectrometry.

In step S2, the dirt load of the rinsing or detergent solution is determined on the basis of the acquired spectral measured values of the dirt components.

And in step S3, wash parameters of a current wash program are adjusted on the basis of the dirt load determined.

Alternatively in step S3, based on the dirt load determined, a detergent is dispensed preferably into the rinsing or detergent solution in the water-conducting household appliance 1.

Although the present invention has been described using exemplary embodiments, it can be modified in a number of ways.

REFERENCE CHARACTERS USED 1 water-conducting household appliance
2 wash tub
3 door
4 washing chamber
5 floor
6 ceiling
7 rear wall
8 side wall
9 side wall
10 loading level
11 rail
12 control device (device for determining the soiling)
13 sensor
14 determination unit
15 adjustment unit
16 spray level
17 pump pot with sump
18 circulating pump
19 heating unit for circulating pump
20 water switch
21 drain pump
22 dosing unit
23 communications interface
24 external server with database
25 fresh water
26 valve
27 heating/cooling unit
28 filter
29 valve
30 measurement housing
31 feed line to lower spray level
32 feed line to middle spray level
33 feed line to upper spray level
A removal direction
E insertion direction
S swivel axis
S1 method step
S2 method step
S3 method step

The invention claimed is:

1. A device for determining a dirt load in a rinsing or detergent solution in a water-conducting household appliance, said device comprising:
   a sensor configured to execute a near-infrared spectroscopy for acquiring spectral measured values of dirt components in the rinsing or detergent solution in the water-conducting household appliance,
   a determination unit configured to determine the dirt load of the rinsing or detergent solution on the basis of the acquired spectral measured values of the dirt components in the rinsing or detergent solution, and
   an adjustment unit configured to adjust a wash parameter of a current wash program in response to the dirt load determined,
   wherein the determination unit is configured to compare output data of the sensor with a predefined calibration model, and the calibration model containing a plurality of different items of spectral information with associated organic compounds, and
   wherein the determination unit provides at least one among a qualitative and a quantitative determination of individual organic compounds identified in the dirt components in the rinsing or detergent solution in the water-conducting household appliance.

2. The device of claim 1 for determining the dirt load in a dishwasher or in a washing machine.

3. The device of claim 1, wherein the sensor is configured to carry out a transmission measurement and/or a reflection measurement.

4. The device of claim 1, wherein the adjustment unit is configured to adjust the current wash program in response to a user input.

5. The device of claim 1, wherein the sensor is configured to measure the organic compounds at a defined temperature.

6. The device of claim 1, wherein the sensor is configured to measure the organic compounds using a correction factor.

7. The device of claim 1, wherein the sensor is disposed in a pump sump of the water-conducting household appliance or in a bypass arrangement inside and/or outside a wash tub of the water-conducting household appliance.

8. A water-conducting household appliance, comprising a device for determining a dirt load in a rinsing or detergent solution in a water-conducting household appliance, said device comprising a sensor configured to execute a near-infrared spectroscopy for acquiring spectral measured values of dirt components in the rinsing or detergent solution in the water-conducting household appliance, a determination unit configured to determine the dirt load of the rinsing or detergent solution in response to the acquired spectral measured values of the dirt components in the rinsing or detergent solution, and an adjustment unit configured to adjust a wash parameter of a current wash program in response to the determined dirt load,
  wherein the determination unit is configured to compare output data of the sensor with a predefined calibration model, and the calibration model containing a plurality of different items of spectral information with associated organic compounds, and
  wherein the determination unit provides at least one among a qualitative and a quantitative determination of individual organic compounds identified in the dirt components in the rinsing or detergent solution in the water-conducting household appliance.

9. The water-conducting household appliance of claim 8, constructed in the form of a dishwasher or a washing machine.

10. The water-conducting household appliance of claim 8, wherein the device is configured to determine a soiling of a wash item, and further comprising an external server, said device configured to communicate with the external server.

11. The water-conducting household appliance of claim 10, wherein the device is configured to communicate the individual organic compounds of the dirt components and/or soiling of the wash item to the external server.

12. The water-conducting household appliance of claim 10 configured to receive a program update from the external server.

13. The water-conducting household appliance of claim 8, further comprising a wash tub and a pump sump, said sensor being disposed in the pump sump or in a bypass arrangement inside and/or outside the wash tub.

14. A method for determining a dirt load in a rinsing or detergent solution in a water-conducting household appliance, said method comprising:
  acquiring spectral measured values of dirt components in the rinsing or detergent solution using near-infrared spectroscopy, and
  comparing the spectral measured values with a predefined calibration model, wherein the calibration model contains a plurality of different items of spectral information with associated organic compounds,
  determining the dirt load of the rinsing or detergent solution on the basis of the acquired spectral measured values of the dirt components, wherein near-infrared spectroscopy provides at least one among a qualitative and a quantitative determination of individual organic compounds identified in the dirt components in the rinsing or detergent solution in the water-conducting household appliance.

15. A method for washing dishes or fabrics in a water-conducting household appliance, said method comprising:
  acquiring spectral measured values of dirt components in a rinsing or detergent solution in the water-conducting household appliance using near-infrared spectroscopy,
  comparing the spectral measured values with a predefined calibration model, wherein the calibration model contains a plurality of different items of spectral information with associated organic compounds,
  determining a dirt load of the rinsing or detergent solution on the basis of the acquired spectral measured values of the dirt components, wherein near-infrared spectroscopy provides a qualitative and quantitative determination of organic compounds identified in the dirt components in the rinsing or detergent solution in the water-conducting household appliance, and
  adjusting a wash parameter of a current wash program in response to the dirt load determined.

16. A method for washing dishes or fabrics in a water-conducting household appliance, said method comprising:
  acquiring spectral measured values of dirt components in a rinsing or detergent solution in the water-conducting household appliance using near-infrared spectroscopy,
  determining the dirt load of the rinsing or detergent solution on the basis of the acquired spectral measured values of the dirt components, wherein near-infrared spectroscopy provides a qualitative and quantitative determination of organic compounds identified in the dirt components in the rinsing or detergent solution in the water-conducting household appliance, and
  dosing a detergent in response to the dirt load determined.

17. The method of claim 16, wherein the detergent comprises a multicomponent detergent product format comprising at least two detergent formulations selected from the group consisting of a first detergent formulation containing at least one constituent having a detergent action on starchy soilings, a second detergent formulation containing at least one constituent having a detergent action on protein soilings, and a third detergent formulation containing at least one constituent having a detergent action on fatty soilings,
  wherein the detergent is dosed such that each of the detergent formulations is dispensed on the basis of a type and amount of the dirt components determined.

18. The method of claim 17, wherein the detergent formulations are liquid.

19. The method of claim 17, wherein the at least one constituent of the first detergent formulation is amylase.

20. The method of claim 17, wherein the least one constituent of the second detergent formulation is protease.

21. The method of claim 17, wherein the least one constituent of the third detergent formulation is a lipase or at least one nonionic surfactant.

22. The method of claim 17, wherein the multicomponent detergent product format comprises the first, second and third detergent formulations.

23. The method of claim 17, further comprising packaging the multicomponent detergent product format in the form of separate accommodation compartments, with each of the compartments containing one of the detergent formulations.

24. The method of claim 23, wherein the accommodation compartments are formed in a cartridge having at least two of said accommodation compartments.

25. The method of claim 24, further comprising dispensing the detergent via a dosing system for multiple dosing of detergents, with the dosing system comprising the first, second and third detergent formulations, the cartridge having the separate accommodation compartments for containing the detergent formulations, and a dosing device connectable to the cartridge.

26. A device for determining a dirt load in a rinsing or detergent solution in a water-conducting household appliance, said device comprising:
- a sensor configured to execute a near-infrared spectroscopy for acquiring spectral measured values of a plurality of different dirt components in the rinsing or detergent solution in the water-conducting household appliance,
- a determination unit configured to determine the dirt load of the rinsing or detergent solution on the basis of the acquired spectral measured values of the plurality of different dirt components in the rinsing or detergent solution, the plurality of different dirt components within the dirt load being organic compounds including fat, protein, and starch, and
- an adjustment unit configured to adjust a wash parameter of a current wash program in response to the dirt load determined.

* * * * *